(12) United States Patent
Rosenblatt et al.

(10) Patent No.: US 9,987,329 B2
(45) Date of Patent: Jun. 5, 2018

(54) METHODS FOR TREATING PERIPHERAL NERVE DAMAGE

(71) Applicant: Cornell University, Ithaca, NY (US)

(72) Inventors: Mark Rosenblatt, New York, NY (US); Victor H. Guaiquil, Bronx, NY (US); Zan Pan, New York, NY (US); Natalia Karagianni, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days. days.

(21) Appl. No.: 15/124,986

(22) PCT Filed: Mar. 12, 2015

(86) PCT No.: PCT/US2015/020232
§ 371 (c)(1),
(2) Date: Sep. 9, 2016

(87) PCT Pub. No.: WO2015/138761
PCT Pub. Date: Sep. 17, 2015

(65) Prior Publication Data
US 2017/0020961 A1  Jan. 26, 2017

Related U.S. Application Data

(60) Provisional application No. 61/951,963, filed on Mar. 12, 2014.

(51) Int. Cl.
*A61K 38/18* (2006.01)
*A61K 9/00* (2006.01)

(52) U.S. Cl.
CPC ........ *A61K 38/1866* (2013.01); *A61K 9/0048* (2013.01)

(58) Field of Classification Search
None
See application file for complete search history.

(56) References Cited

U.S. PATENT DOCUMENTS 7,125,856 B1   10/2006  Isner
2011/0318365 A1  12/2011  Li

OTHER PUBLICATIONS

Dhondt et al., "Neuronal FLT1 Receptor and Its Selective Ligand VEGF-B Protect Against Retrograde Degeneration of Sensory Neurons," The FASEB Journal, 2011, 25:1461-1473.
Pan et al., "Vascular Endothelial Growth Factor Promotes Anatomical and Functional Recovery of Injured Peripheral Nerves in the Avascular Cornea," The FASEB Journal, 2013, 27:2756-2767.
Zhang et al., "VEGF-B is Dispensable for Blood Vessel Growth but Critical for Their Survival, and VEGF-B Targeting Inhibits Pathological Angiogenesis," PNAS, 2009, 106(15):6152-6157.
PCT International Search Report for PCT Application No. PCT/US2015/020232 dated Jul. 20, 2015 (3 pages).

*Primary Examiner* — John D Ulm
(74) *Attorney, Agent, or Firm* — Eversheds Sutherland (US) LLP

(57) ABSTRACT

VEGF-B, as well as a combination of VEGF-B and VEGF-A, mediates peripheral nerve repair. Methods to treat damage to the peripheral nervous system are described.

21 Claims, 19 Drawing Sheets

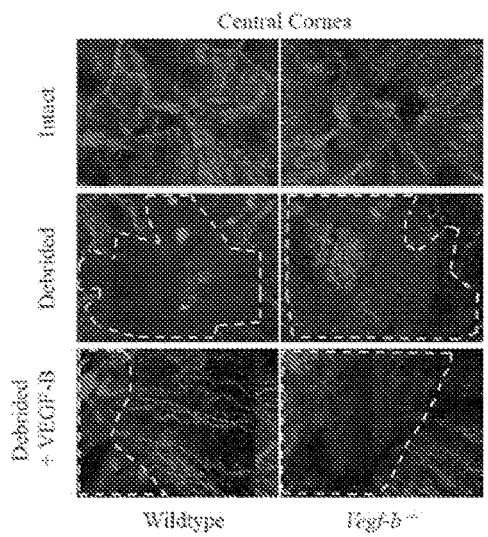
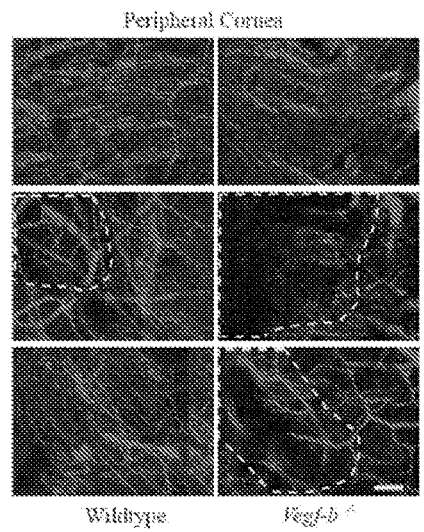
FIGURE 4A                FIGURE 4B
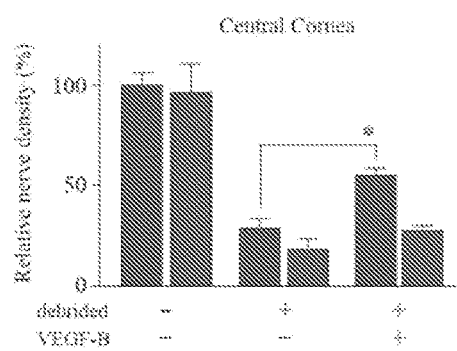
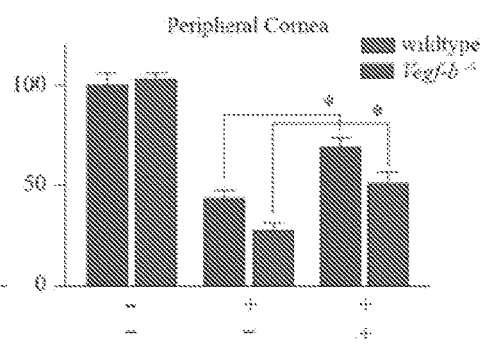
FIGURE 4C                FIGURE 4D

SEQUENCE LISTING

<160> NUMBER OF SEQ ID NOS: 2

<210> SEQ ID NO 1
<211> LENGTH: 207
<212> TYPE: PRT
<213> ORGANISM: Homo sapiens

<400> SEQUENCE: 1

Met Ser Pro Leu Leu Arg Arg Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
        195                 200                 205

<210> SEQ ID NO 2
<211> LENGTH: 232
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Val Lys Phe Met Asp Val Tyr Gln Arg Ser Tyr Cys His
            20                  25                  30

Pro Ile Glu Thr Leu Val Asp Ile Phe Gln Glu Tyr Pro Asp Glu Ile
        35                  40                  45

Glu Tyr Ile Phe Lys Pro Ser Cys Val Pro Leu Met Arg Cys Gly Gly
50                  55                  60

Cys Cys Asn Asp Glu Gly Leu Glu Cys Val Pro Thr Glu Glu Ser Asn
65                  70                  75                  80

Ile Thr Met Gln Ile Met Arg Ile Lys Pro His Gln Gly Gln His Ile
            85                  90                  95

Gly Glu Met Ser Phe Leu Gln His Asn Lys Cys Glu Cys Arg Pro Lys
        100                 105                 110

Lys Asp Arg Ala Arg Gln Glu Lys Lys Ser Val Arg Gly Lys Gly Lys
    115                 120                 125

Gly Gln Lys Arg Lys Arg Lys Lys Ser Arg Tyr Lys Ser Trp Ser Val
130                 135                 140

Tyr Val Gly Ala Arg Cys Cys Leu Met Pro Trp Ser Leu Pro Gly Pro
145                 150                 155                 160

```
His Pro Cys Gly Pro Cys Ser Glu Arg Arg Lys His Leu Phe Val Gln
            165                 170                 175

Asp Pro Gln Thr Cys Lys Cys Ser Cys Lys Asn Thr Asp Ser Arg Cys
            180                 185                 190

Lys Ala Arg Gln Leu Glu Leu Asn Glu Arg Thr Cys Arg Cys Asp Lys
        195                 200                 205

Pro Arg Arg His Ala Lys Trp Ser Gln Ala Ala Pro Met Ala Glu Gly
    210                 215                 220

Gly Gly Gln Asn His His Glu Val
225                 230
```

METHODS FOR TREATING PERIPHERAL NERVE DAMAGE

CROSS REFERENCE TO RELATED APPLICATIONS

This application claims the priority benefit of PCT/US2015/020232 filed on Mar. 12, 2015 which claims priority benefit to U.S. Provisional Patent Application No. 61/951,963, filed Mar. 12, 2014. The contents of these applications are hereby incorporated by reference in their entirety.

GOVERNMENT FUNDING

This invention was made with Government support under Grant Numbers EY018594 and EY015829 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 1, 2015, is named 31305_0037_SL.txt and is 4,143 bytes in size.

FIELD OF INVENTION

Embodiments of the invention generally relate to methods for treating peripheral nerve damage. More specifically, the disclosure relates to the use of VEGF to treat peripheral nerve damage.

BACKGROUND

Nerves can be damaged either through trauma or disease. Nerves from the peripheral nervous system (PNS) have significantly greater capacity to regenerate and reinnervate their original targets after injury, as compared to nerves from central nervous system (CNS). The successful regeneration of PNS neurons requires a number of intrinsic and extrinsic factors, as well as, a permissive microenvironment for axonal regrowth. Bosse, E. *Extrinsic cellular and molecular mediators of peripheral axonal regeneration*, Cell Tissue Res. 349, 5-14 (2012). Among the numerous growth factors able to induce nerve regeneration, the family of vascular endothelial growth factors (VEGF), has been implicated as a potent mediator of developmental neurogenesis and adult nerve regeneration. Carmeliet, P. & Carmen Rde, A, *VEGF ligands and receptors: implications in neurodevelopment and neurodegeneration*, Cellular and Molecular Life Sciences: CMLS 70, 1763-1778 (2013); Licht, T. & Keshet, E., *Delineating multiple functions of VEGF-A in the adult brain*, Cellular and Molecular Life Sciences: CMLS 70, 1727-1737 (2013); Mackenzie, F. & Ruhrberg, C., *Diverse roles for VEGF-A in the nervous system*, Development 139, 1371-1380 (2012).

VEGF-A, is a well-characterized and potent angiogenic factor, but is also a strong inducer of nerve growth. Several studies have demonstrated that both VEGF-A and -B are expressed during peripheral nerve injury. Li, X., Kumar et al., *Complicated life, complicated VEGF-B*, Trends Mol. Med. 18, 119-127 (2012); and Carmeliet, P. & Carmen Rde, A, *VEGF ligands and receptors: implications in neurodevelopment and neurodegeneration*, Cellular and Molecular Life Sciences: CMLS 70, 1763-1778 (2013) In the setting of injury, VEGF-B plays a role in cell survival, nerve protection and growth. Li, X., Kumar et al. (2012); and Dhondt, J. et al., *Neuronal FLT1 receptor and its selective ligand VEGF-B protect against retrograde degeneration of sensory neurons*, FASEB J. 25, 1461-1473 (2011).

The survival effect of VEGF-B on brain cortical neurons, retinal neurons and motor neurons in the spinal cord, is indicative of its pleiotropic role. Li, X., Kumar et al., Trends Mol. Med. 18, 119-127 (2012). VEGF-B treatment has also been found to reduce stroke volume in a middle cerebral artery ligation model and increased survival of retinal ganglion cells in an optic nerve crush injury model, and VEGF-B knockout mice suffered severe strokes and exacerbated retinal ganglion cell death in both injury models. Li, Y. et al., *VEGF-B inhibits apoptosis via VEGFR-1-mediated suppression of the expression of BH3-only protein genes in mice and rats*, The Journal of Clinical Investigation 118, 913-923 (2008); Sun, Y. et al., *Increased severity of cerebral ischemic injury in vascular endothelial growth factor-B-deficient mice*, J. Cereb. Blood Flow Metab. 24, 1146-1152 (2004); Greenberg, D. A. & Jin, K., *Vascular endothelial growth factors (VEGFs) and stroke*, Cellular and Molecular Life Sciences:CMLS 70, 1753-1761 (2013).

VEGF-B has also been used with promising results in Parkinson's disease and amyotrophic lateral sclerosis models. Falk, T. et al., *Vascular endothelial growth factor-B is neuroprotective in an in vivo rat model of Parkinson's disease*, Neurosci. Lett. 496, 43-47 (2011); Poesen, K. et al., *Novel role for vascular endothelial growth factor (VEGF) receptor-1 and its ligand VEGF-B in motor neuron degeneration*, J. Neurosci. 28, 10451-10459 (2008).

Given the ability of VEGF-B to regulate both vascular endothelial cells (angiogenesis) as well as axonal growth and survival following injury, it is unclear whether VEGF-B exerts its effects on nerve regeneration through the increase in blood supply, or through direct effects on nerve tissue. Nash, A. D. et al., *The biology of vascular endothelial growth factor-B (VEGF-B)*, Pulm. Pharmacol. Ther. 19, 61-69 (2006); Sun, Y. et al., *Vascular endothelial growth factor-B (VEGFB) stimulates neurogenesis: evidence from knockout mice and growth factor administration*, Dev. Biol. 289, 329-335 (2006). Indeed, specific studies on its role on peripheral neurons independent of its vascular role are lacking. We have previously reported that VEGF-A can stimulate trigeminal neuronal cell growth and enhance cornea nerve regeneration, resulting in anatomical and functional recovery of peripheral injured nerves independently of its angiogenic effects. Pan, Z., Fukuoka et al., *Vascular endothelial growth factor promotes anatomical and functional recovery of injured peripheral nerves in the avascular cornea*, FASEB J, 27, 2756-2767 (2013).

SUMMARY OF INVENTION

This summary is provided to introduce a selection of concepts that are described in further detail below. This summary is not intended to identify key or essential features of the invention, nor is it intended to be construed as being limited to the exemplified embodiments described herein.

Provided herein are methods for treating damage to the peripheral nervous system, including administering VEGF-B to a subject in need thereof. In some embodiments, the VEGF-B may be administered in combination with VEGF-A. In further embodiments, the methods may include a second administration of VEGF-B or VEGF-A following the first administration of VEGF-B (alone or in combination with VEGF-A). The damage to the peripheral nervous system may be trauma caused by accident, surgery, a neurotoxin, or a neurodegenerative disease. The treated neurons may undergo dendrite growth or branching; an axon may be regenerated. The VEGF may be administered as a protein or as a gene therapy, in a pharmaceutical composition by topical application, at a location of the nerve damage, or by intravenous injection.

Provided are methods for treating peripheral nerve damage in a subject, comprising: administering VEGF-B to the subject having the nerve damage in an amount effective to treat the peripheral nerve damage by stimulating nerve growth at a location of the nerve damage. In some embodiments, the VEGF-B may be administered to the subject in combination with VEGF-A. The methods may also comprise, after the administering of the VEGF-B, a second administration to the subject of a second effective amount of VEGF-B or of VEGF-A. The second administration may take place after one or more seconds, or after one or more minutes, or even after a number of days (e.g., 1 or 2 days) following the first administration of VEGF-B. In embodiments, the peripheral nerve damage may be neuritis.

Embodiments also relate to methods for treating ocular nerve damage in a subject, comprising: administering an effective amount of VEGF-B to a subject suffering from the ocular nerve damage. In some embodiments, the nerve damage may be neuritis. The VEGF-B may likewise be administered to the subject in combination with VEGF-A, as well as other suitable pharmaceutical excipients. The methods may also comprise, after the administering of the VEGF-B, a second administration to the subject of a second effective amount of VEGF-B or of VEGF-A. The second administration may take place after one or more seconds, or after one or more minutes, or even after a number of days (e.g., 1 or 2 days) following the first administration of VEGF-B. In certain embodiments, the second administration is of a second effective amount of VEGF-B. The VEGF-B may be administered to the subject suffering from the ocular damage by topical application, injection, or implantation in or on the subject's eye.

BRIEF DESCRIPTION OF DRAWINGS

The manner in which objectives of the present disclosure and other desirable characteristics may be obtained will become further evident from the following description and the various figures submitted herewith.

FIG. 3 shows an increase in endogenous VEGF-B expression after peripheral nerve injury. The peripheral nerve endings that innervate the cornea were injured in C57BL/6 mice by central corneal epithelial debridement.

FIG. 6A shows that re-epithelization was accelerated in both groups of VEGF-B treated mice, but the epithelium healed rapidly in wild type mice. Quantification of the images confirms that epithelial wound closure is accelerated upon VEGF-B treatment.

DETAILED DESCRIPTION

Figure 1A:
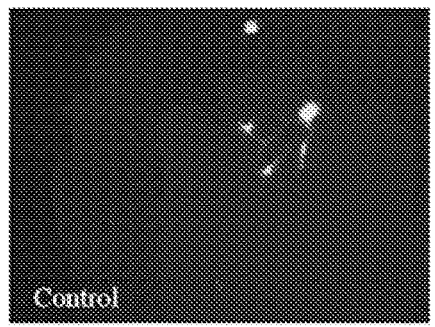
FIG. 1 shows VEGF-B induced neurite growth and survival on trigeminal ganglion neurons via VEGFR1 and NRP1. Neurons from trigeminal ganglia of thy1-YFP mice were isolated and cultured as indicated in Material and Methods. After 3 days in culture, few neurites grew in neurons cultured only in medium (FIG. 1A). Addition of VEGF-B immediately after plating the cells induced long and extensive branching of neurites (FIG. 1B). The neurite growth was competitively inhibited by soluble VEGFR1 at an equimolar dose (FIG. 1C) or by antibodies against VEGFR1 (FIG. 1D) or neuropilin1 (FIG. 1F), but not by antibodies against VEGFR2 (FIG. 1E). Quantification analysis of neurite length demonstrated that the VEGF-B induced growth requires activation of VEGFR1 and NRP1 (FIG. 1G). The effect of VEGF-B on neuronal survival, analyzed as described in materials and methods, showed that there was a time dependent cell death of TG neurons after 3 days in culture and only 25% of neurons were found viable at this time point (FIG. 1H). However, neuronal viability increased to 50% when cells were treated with a single dose of 50 ng/ml of VEGF-B (FIG. 1H). Data represent the mean±SEM, n=3, and a P value <0.05 was considered statistically significant between the treatments. Scale bar=50 μm.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Discussed in further detail herein, in reference to the various experiments blow and supporting data presented in the attached Figures, it has been found that: (1) peripheral nerve regeneration is impaired in mice lacking VEGF-B, (2) VEGF-B can restore the anatomic and function innervation of target tissues by induction of nerve growth and nerve regeneration, (3) the effects of VEGF-B are specific for injured nerves and are independent of any vascular effect, (4) that the effects of VEGF-B on nerve regeneration are distinct from those observed for VEGF-A, and (5) VEGF-B and VEGF-A in combination have a surprising and synergistic effect on nerve regeneration. The effect of VEGF-B on neuronal growth and peripheral nerve regeneration was evaluated independently of its angiogenic effect, by specifically using isolated trigeminal ganglia neurons and the cornea as a model that not only contains the highest density of sensory innervation of the human body, but also is avascular.

VEGF-B induced extensive neurite growth in isolated trigeminal ganglia neurons, a finding that has not been described before. The effects of VEGF-B on total neurite extension were comparable to that seen for VEGF-A. However, a closer examination of VEGF-B effects demonstrated a dramatically enhanced induction on neurite branching when compared to VEGF-A. This differential effect of VEGF-B on branching could be partially explained by our finding that VEGF-B signaling requires the activation of both VEGFR-1 and NRP1. It has been previously shown that VEGF-A action on trigeminal neurons requires concomitant activation of VEGFR2 in addition to VEGFR1 and NRP1. Pan, Z. et al., FASEB J. 27, 2756-2767 (2013). VEGF-B not only promoted neurite extension and branching, but also increased the survival of TG neurons. Thus VEGF-B has dual effects, it protects neurons from death and induces strong neuronal growth.

The in vitro findings lead us to determine whether VEGF-B could play a role on nerve regeneration in vivo. Previous reports indicate that VEGF-B is not fundamental for normal homeostasis but is overexpressed during disease states[6,8,19,20]. (Dhondt, J. et al., *Neuronal FLT1 receptor and its selective ligand VEGF -B protect against retrograde degeneration of sensory neurons*, FASEB J. 25, 1461-1473 (2011); Sun, Y. et al., J. Cereb. Blood Flow Metab. 24, 1146-1152 (2004); Greenberg, D. A. & Jin, K., Cellular and Molecular Life Sciences: CMLS 70, 1753-1761 (2013). Boer, K. et al., *Cellular distribution of vascular endothelial growth factor. A (VEGFA) and B (VEGFB) and VEGF receptors 1 and 2 in focal cortical dysplasia type IIB*, Acta Neuropathol. 115, 683-696 (2008); Xie, L., Mao et al., *Vascular endothelial growth factor-B expression in postischemic rat brain*, Vasc. Cell 5, 8 (2013).

It has also been found that the level of VEGF-B protein expression increases consistently and significantly after injury in the cornea. This increased endogenous expression may play an important physiologic role in nerve repair. Studies using the Vegf-b$^{-/-}$ mice indicated that during normal conditions no outstanding phenotype is seen in these mice. Some cardiac abnormalities and impaired protection against brain ischemic injury have been described. Sun, Y. et al., J. Cereb. Blood Flow Metab. 24, 1146-1152 (2004); Aase, K. et al., *Vascular endothelial growth factor-B-deficient mice display an atrial conduction defect*, Circulation 104, 358-364 (2001); Bellomo, D. et al., *Mice lacking the vascular endothelial growth factor-B gene (Vegfb) have smaller hearts, dysfunctional coronary vasculature, and impaired recovery from cardiac ischemia*, Circ. Res. 86, E29-35 (2000); Mould, A. W. et al., *Vegfb gene knockout mice display reduced pathology and synovial angiogenesis in both antigen-induced and collagen-induced models of arthritis*, Arthritis Rheum. 48, 2660-2669 (2003).

However, when the Vegf-b$^{-/-}$ mice were challenged by superficial nerve injury, they showed a delayed nerve and epithelium recovery compared to wild type mice, indicating that the presence of VEGF-B is necessary for a normal healing response. This requirement of VEGF-B for normal nerve recovery has also been observed in retrograde degeneration of sensory neurons and adult brain neurogenesis. Dhondt, J. et al., FASEB J. 25, 1461-1473 (2011); Sun, Y. et al., Dev. Biol. 289, 329-335 (2006).

The actions of VEGF-B on the vasculature and CNS seem to depend on the presence of disease or injury. Thus, a corneal nerve-wounding model was used to examine the differential effects of VEGF-B on PNS innervation in the absence or presence of nerve injury. This wounding model also excludes any angiogenic influence, due to the avascular nature of the cornea. It was found that the slow release of VEGF-B within the target tissue (intrastromal pellet) or from an adjacent site (subconjunctival) induced nerve regeneration in the injured zone without altering the innervation of healthy tissue. Thus, VEGF-B induced nerve repair of injured nerves in vivo without affecting pre-existing uninjured nerves. Exogenous VEGF-B application accelerated the recovery of the injured nerves not only in wild type mice, but also alleviated the impairment of re-innervation seen in the Vegf-b$^{-/-}$ mice. Importantly, VEGF-B did not produce any unwanted neovascularization (data not shown) while it promoted potent nerve regeneration.

Investigations were conducted to determine whether the improvement in anatomic reinnervation of the PNS in response to VEGF-B was accompanied by an improvement in PNS function at the target tissue. It was observed that the faster regeneration observed in the injured nerves upon VEGF-B treatment, was accompanied by improved cornea sensation in these animals. Sensory neurons of the PNS may have functions beyond sensation, including trophic influences on target tissues. VEGF-B also induced accelerated re-epithelization of the debrided epithelium in the cornea in wild type and reversed the delay in re-epithelization in Vegf-b$^{-/-}$ mice. This effect of VEGF-B on the epithelial wound healing seems to be indirect, resulted from the neurotrophic effect rather than the direct action on epithelial cells, since our epithelial scratch assays demonstrated that VEGF-B treatment induced no improvement in the wound closure in cultured corneal epithelial cells. This data suggest that VEGF-B mediated nerve regeneration restores not only sensation, but also restores the critical trophic function of PNS sensory nerves.

Taken together, the data demonstrates that VEGF-B is required for proper nerve regeneration in the cornea. The increased endogenous VEGF-B expression in response to injury or the application of exogenous VEGF-B promotes nerve regeneration without affecting undamaged nerves or inducing unwanted neovascularization. VEGF-B mediated nerve regeneration restored the sensation and healing responses of PNS innervated tissues. The relative inactivity of VEGF-B on intact neurons, its lack of significant angiogenic activity and its potent action in restoring PNS function to damaged tissues make VEGF-B an important therapeutic target for treating injured peripheral nerves.

Figure 11:
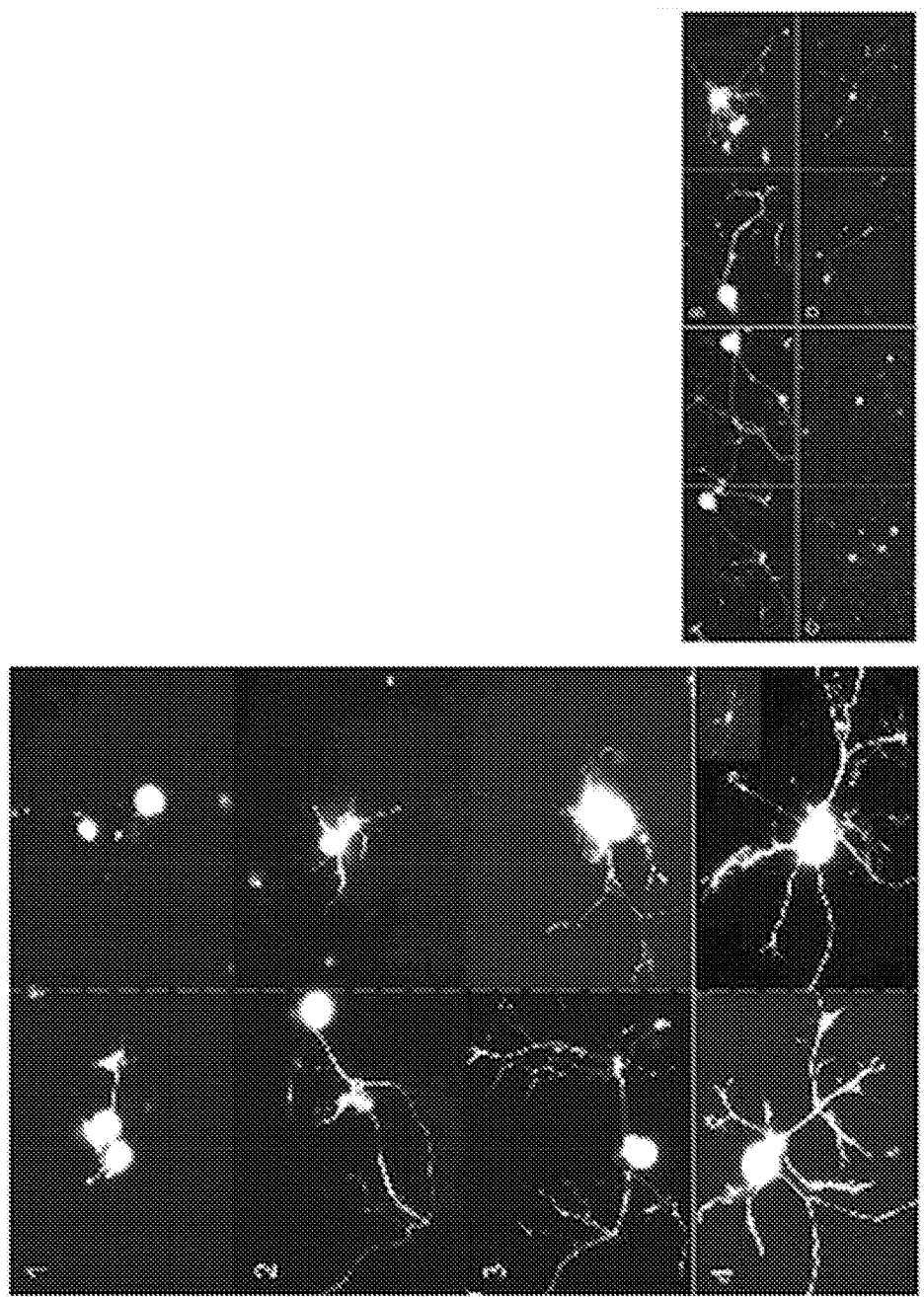
FIG. 11 includes images showing neurons taken from primary neuronal cultures (VEGF-B rescue project). The left column shows neurons from the four different cultures taken on the 4th culture day, and the right column includes images taken on the 6th culture day. As further shown by the images of FIGS. 11A-11D, neurons treated with VEGF-B on three consecutive days present with longer dendrites and more branches on day 6.

When VEGF-A is used in combination with VEGF-B, we have observed greater neuronal growth both in vitro and in vivo. In mice, the combinatorial treatment results in improved neuro-regeneration of peripheral nerves, with concomitant recovery of sensation and trophic functions. This combinatorial treatment of VEGF-A plus VEGF-B results in better therapeutics than either agent alone as seen in the in vitro data shown in FIG. 11.

Figure 12:
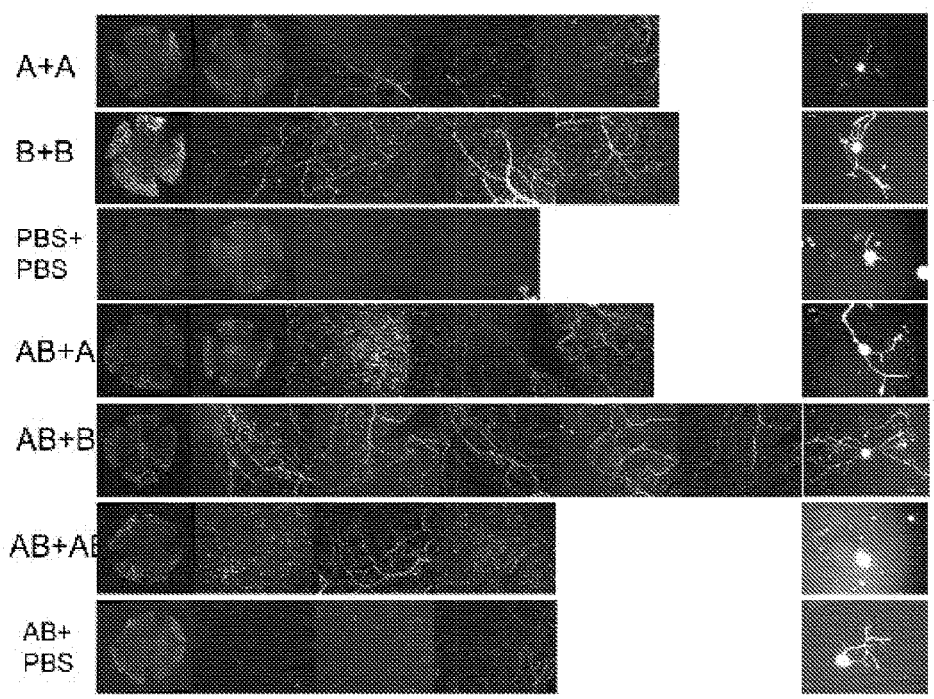
FIG. 12 Includes a comparison of images showing the results of treatment of primary neuronal cultures with various combinations of VEGF-A, VEGF-B, and controls, as labeled.

In mice the use of both VEGF-A plus VEGF-B induced a greater nerve regeneration of injured nerves, as well as greater neuronal growth in isolated peripheral neurons than any other therapeutic combination as shown in FIG. 12. In embodiments of the invention, VEGF-B may be administered in combination with VEGF-A either systemically or to sites of injury. Given the preference for promoting regeneration only at sites of injury, systemic administration for peripheral nerve damage that is pervasive or difficult to access may be a viable approach. Therefore, embodiments of the invention generally relate to administering VEGF-B, or a combination of VEGF-B and VEGF-A, at regions of peripheral nerve injury. Embodiments of the invention also relate to methods for treating peripheral ocular nerve injury, particularly peripheral nerve injury in the cornea. In such embodiments, administration of the active ingredients may be topical or through an injection. Similar modes of administration may also be suitable at other regions of peripheral nerve injury.

Subjects

The subject may be any animal, including a human. human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

Preferred subjects include human subjects suffering from damage to the peripheral nervous system. The subject is generally diagnosed with the condition of the subject invention by skilled artisans, such as a medical practitioner.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof. The term subject includes a subject of any body height, body weight, or any organ or body part size or shape.

Diseases and Conditions

Methods described in the various embodiments herein relate to treating peripheral nerve injuries by, inter alia, administering VEGF-A, or VEGF-A plus VEGF-B, to treat peripheral nerve injuries in a myriad of target organs and tissues. Diseases and conditions treated by the methods may therefore include treatment of PNS nerve trauma in subjects that is caused by accident, surgery, or neurotoxin, or by infection, inflammation, or genetic nerve degeneration. In certain embodiments, a disease or condition treated by the methods is an ocular nerve injury, such as, for example, an injury to the cornea.

VEGF-A and VEGF-B Proteins

VEGF-B is the 207 amino acid protein described in GenBank: AGC09607.1 with amino acid sequence:

```
                                                        (SEQ ID NO: 1)
  1   mspllrrlll aallqlapaq apvsqpdapg hqrkvvswid vytratcqpr evvvpltvel 61   mgtvakqlvp scvtvqrcgg ccpddglecv ptgqhqvrmq ilmirypssq lgemsleehs 121   qcecrpkkkd savkpdraat phhrpqprsv pgwdsapgap spadithptp apgpsahaap 181   sttsaltpgp aaaaadaaas svakgga
``` and variants thereof with conservative amino acid substitutions or substantially the same amino acid sequence, and other variants as described below.

VEGF-A is the 232 amino acid protein described in NextProt entry NX_P15692 with amino acid sequence:

```
                                                        (SEQ ID NO. 2)
  1   MNFLLSWVHW SLALLLYLHVKFMDVYQRS

51   YCHPIETLVD IFQEYPDEIE YIFKPSCVPL MRCGGCCNDE GLECVPTEES

101   NITMQIMRIK PHQGQHIGEM SFLQHNKCEC RPKKDRARQE KKSVRGKGKG
```

```
                           -continued
151  QKRKRKKSRY KSWSVYVGAR CCLMPWSLPG PHPCGPCSER RKHLFVQDPQ

201  TCKCSCKNTD SRCKARQLEL NERTCRCDKP RRH AKWSQAAPMA EGGGQNHHEV
``` and variants thereof with conservative amino acid substitutions or substantially the same amino acid sequence, and other variants as described below.

A "conservative amino acid substitution" refers to the replacement of one amino acid residue by another chemically similar amino acid residue, or functional fragments of VEGF-B and VEGF-A. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid); substitution of one aromatic amino acid (tryptophan, tyrosine, or phenylalanine) for another.

Those of skill in the art will recognize that in other useful VEGF-A and VEGF-B proteins can be substituted with other, chemically, sterically and/or electronically similar residues without substantially altering VEGF-A or VEGF-B biological activity.

As employed herein, the term "substantially the same amino acid sequence" refers to amino acid sequences having at least about 60% sequence homology or identity with respect to any of the amino acid sequences described herein ("reference sequences"), and retaining comparable functional and biological activity characteristic of the protein defined by the reference sequences described, particularly with respect to neoplastic cellular proliferation and/or transformation or its inhibition. More preferably, proteins having "substantially the same amino acid sequence" will have at least about 80%, still more preferably about 90% amino acid identity with respect to a reference amino acid sequence; with greater than about 95% amino acid sequence identity being especially preferred. It is recognized, however, that polypeptide containing less than the described levels of sequence identity arising as splice variants or that are modified by conservative amino acid substitutions are also encompassed within the scope of the present invention. The degree of sequence homology is determined by conducting an amino acid sequence similarity search of a protein data base, such as the database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine. See, for example: Altchul, S. F. et al., *Gapped BLAST and PSI-BLAST: a new generation of protein database search programs*. Nucleic Acids Res. 25(17):3389-402 (1997); Zhang, J., & Madden, T. L., *PowerBLAST: a new network BLAST application for interactive or automated sequence analysis and annotation*, Genome Res. 7(6):649-56 (1997); Madden, T. L. et al., *Applications of network BLAST server*, Methods Enzymol. 266:131-4(1996); Altschul, S. F. et al., *Basic local alignment search tool*, J. Mol. Biol. 215(3):403-10 (1990).

Also encompassed by the terms VEGF-A and VEGF-B respectively, are biologically functional or active peptide analogs thereof. The term peptide "analog" includes any polypeptide having an amino acid residue sequence substantially identical to a sequence specifically shown herein in which one or more residues have been conservatively substituted with a functionally similar residue and which displays the ability to mimic the biological activity of VEGF-A or VEGF-B respectively, particularly with respect to the ability to promote neuroregeneration, dendrite sprouting, or branching, as described herein above. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue, provided that such polypeptide displays the requisite biological activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The inventive polypeptide of the present invention also include any polypeptide having one or more additions and/or deletions of residues, relative to the sequence of a polypeptide whose sequence is shown herein, so long as the requisite VEGF-A or VEGF-B biological activity is maintained.

VEGF-A and VEGF-B Gene Therapies

The sequences of VEGF-A and VEGF-B are known in the art, as are methods of incorporating VEGF-A and VEGF-B into expression vectors suitable for gene therapy, as are means of delivering gene therapies to subjects.

Pharmaceutical Compositions

The present invention also provides a method for the treatment of a disease or condition characterized by peripheral nerve damage in a subject, by administering to the subject a composition comprising a therapeutically effective amount of VEGF-B, or a combination of VEGF-B and VEGF-A, and a pharmaceutically acceptable excipient.

In another aspect, the present invention provides pharmaceutically acceptable compositions which comprise a therapeutically-effective amount of VEGF-B, or a combination of VEGF-B and VEGF-A as described above, formulated together with one or more pharmaceutically acceptable excipients. In another aspect, the present invention provides pharmaceutically acceptable compositions which comprise a therapeutically-effective amount of one or more of VEGF-B, or a combination of VEGF-B and VEGF-A as described above, formulated together with one or more pharmaceutically acceptable excipients and other therapeutically effective medications known in the art allowing for (but not limited to) combination therapies to improve overall efficacy of each individual therapeutic, or to limit the concentration of either therapeutic to avoid side effects and maintain efficacy.

In addition to being suitable for administration as proteins or through gene therapy, the active ingredient(s) and excipient(s) may be formulated into compositions and dosage forms according to methods known in the art. As described in detail below, the pharmaceutical compositions of the present invention may be specially formulated for administration in solid or liquid form, including those adapted for the following: (1) parenteral administration, for example, by subcutaneous, intramuscular or intravenous injection as, for example, a sterile solution or suspension; (2) sublingually or buccally; (3) ocularly; or (4) nasally.

The active ingredient(s) may therefore be formulated for topical (including ocular) application or as an injectable.

In embodiments, it is generally advantageous to formulate parenteral compositions in dosage unit form for ease of administration and uniformity of dosage. The dosage unit forms are dictated by, and directly dependent on (a) the unique characteristics of the active compound (VEGF) and the particular therapeutic effect to be achieved, and (b) any limitations inherent in the art of compounding such an active compound for the treatment of peripheral nerve damage and, specifically, nerve damage (or injury) to the cornea.

Data obtained from cell culture assays and animal studies can be used in formulating a range of dosages for use in humans or other animals. Specifically, the dosage of the active compound(s) preferably lies within a range of circulating concentrations that is therapeutically effective, with little or no toxicity to the subject of the treatment. Persons skilled in the art will readily appreciate that dosage ranges may vary depending on the dosage form employed, and the route of administration utilized. Moreover, the dosage may be adjusted depending on the subject's weight, age, health, and tolerance for the compound or composition administered by the methods described herein.

As used herein, an "effective amount" of VEGF ligand(s), or a "therapeutically effective amount" of the pharmaceutical composition comprising VEGF ligands(s), means an amount that is "effective" at dosages and for periods of time necessary to achieve the desired result. Specifically, an "effective amount" means an amount that is sufficient to treat a disease or condition characterized by symptoms comprising peripheral nerve damage. The dosage of active ingredient(s) may vary, depending on the reason for use and the individual subject. The dosage may be adjusted based on the subject's weight, the age and health of the subject, and tolerance for the compound or composition.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in Remington's Pharmaceutical Sciences, *The Science and Practice of Pharmacy*, 19th Ed., Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

In methods described herein, the VEGF-B, or the combination of VEGF B and VEGF-A, may be administered in the form of small molecules. Examples of such small molecules include, but are not limited to, peptides, peptidomimetics, amino acids, amino acid analogs, polynucleotides, polynucleotide analogs, nucleotides, nucleotide analogs, organic or inorganic compounds, salts, esters, and other pharmaceutically acceptable forms of such compounds. It is understood that appropriate doses of small molecule agents are dependent upon a number of factors that are within the scope of knowledge of the ordinarily skilled physician, veterinarian, or researcher. That is, dose(s) of the small molecule will vary, depending on, for example, the identity, size, and condition of the subject being treated, as well as the route by which the composition is to be administered (if applicable), and the effect which the practitioner desires the small molecule to have upon the nucleic acid or polypeptide.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition may be increased by the addition of a disintegrant to the composition. Disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, the VEGF-B, or a combination of VEGF-B and VEGF-A, and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

A blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Recently, the pharmaceutical industry introduced microemulsification technology to improve bioavailability of some lipophilic (water insoluble) pharmaceutical agents. Examples include (but are not limited to) Trimetrine (Dordunoo, S. K. et al., Drug Development and Industrial Pharmacy, 17(12), 1685-1713 (1991)) and REV 5901 (Sheen, P. C. et al., J. Pharm. Sci. 80(7), 712-714 (1991)). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, preferred carriers will generally include those that have Generally-Recognized-as-Safe (GRAS) status, and that can both solubilize the compound of the present invention and microemulsify it at a later stage when the solution comes into contact with a complex water phase (such as found in the human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Specific examples include polyethylene-glycolized fatty glycerides and polyethylene glycols.

In certain embodiments, amphiphilic carriers may be saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids. A fatty acid composition particularly suitable for use in certain embodiments may include capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are alsocontemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in embodiments of the invention may include those that are readily water-soluble, can be covalently attached to a vesicle-forming lipid, and are tolerated in vivo without toxic effects (i.e., are biocompatible). For example, suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In certain embodiments, the polymer may be polyethyleneglycol having a molecular weight of from about 100 to about 5,000 daltons, and more preferably having a molecular weight of from about 300 to about 5,000 daltons. In further embodiment, the polymer may be polyethyleneglycol of 750 daltons (PEG(750)). Polymers may also be selected based on the number of monomers therein, as certain embodiments preferably utilize polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta, or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al., Plant Cell Tiss. Org. Cult. 38:1-3-113 (1994)). The complexation takes place by Van der Waals interactions and by hydrogen bond formation. For a general review of the chemistry of cyclodextrins, see Wenz, Agnew., Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, U.S. Pat. No. 3,453,259 to Parmeter (I) et al., U.S. Pat. No. 3,453,257 to Parmeter (II) et al., and U.S. Pat. No. 3,459,731 to Gramera et al. (all of which being incorporated by reference herein in their entirety) describe electroneutral cyclodextrins. Other derivatives may include cyclodextrins with cationic properties as described in Parmeter (II) et al. (incorporated by reference herein in its entirety), insoluble crosslinked cyclodextrins as described in U.S. Pat. No. 3,420,788 to Solms (incorporated by reference herein in its entirety), and cyclodextrins with anionic properties as described in U.S. Pat. No. 3,426,011 to Parmeter (III) (incorporated by reference herein in its entirety. As further described in Parmeter (III), among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin. Furthermore, sulfoalkyl ether cyclodextrin derivatives are described in U.S. Pat. No. 5,134,127 to Stella et al. (incorporated by reference herein in its entirety). Stella, et al.

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 nm in diameter; large unilamellar vesicles (LUVS) are typically larger than 0.05 nm Oligolamellar large vesicles and multilamellar vesicles have multiple, usually concentric, membrane layers and are typically larger than 0.1 nm. Liposomes with several non-concentric membranes, i.e., several smaller vesicles contained within a larger vesicle, are termed multivesicular vesicles.

In certain embodiments, the invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. Compounds for use in embodiments of the invention may be aggregated with a lipid surfactant and carried within the liposomes internal space. In such embodiments, the liposome membrane is preferably formulated to resist the disruptive effects of the active agent-surfactant aggregate. According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871 and Published PCT Application WO 96/14057, the disclosures of which are hereby incorporated by reference herein in their entireties; and New RRC, Liposomes. A practical approach, IRL Press, Oxford (1990), pages 33-104; Lasic D D, *Liposomes from physics to applications*, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidyl-choline or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (incorporated by reference herein in its entirety).

The release characteristics of a formulation of the present invention depend on the encapsulating material, the concentration of encapsulated drug, and the presence of release modifiers. Multiple coatings or mixtures of cyanamide encapsulated in different materials can be used to obtain an initial release, followed by later release. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween.®. and Pluronic.®. Pore forming agents which add microstructure to the matrices (i.e., water soluble compounds such as inorganic salts and sugars) are added as particulates. The range should be between one and thirty percent (w/w polymer).

EXAMPLES

The present description is further illustrated by the following examples, which should not be construed as limiting in any way. The contents of all cited references (including literature references, issued patents, published patent applications as cited throughout this application) are hereby expressly incorporated by reference.

Animals

All experiments were performed according to the guidelines of the Association for Research in Vision and Ophthalmology Statement for the Use of Animals in Ophthalmic and Vision Research and been approved by the Institution Animal Care and Use Committee of Weill Cornell Medical College, in accordance with the U.S. National Institutes of Health Guide for the Care and Use of Laboratory Animals. The C57BL/6 and the neurofluorescent thy1-YFP mice were purchased from Jackson Laboratories and the VEGF-B knockout (Vegf-b$^{-/-}$) mice were a generous gift from Dr. David A. Greenberg (Buck Institute for Research on Aging). All mice were fed a standard diet ad libitum and maintained on a 12-h light-dark cycle. For survival experiments, 6-9 weeks old mice were anesthetized intraperitoneally with a combination of ketamine (10 mg/kg) and xylazine (1 mg/kg; Phoenix Scientific) and then a drop of proparacaine hydrochloride ophthalmic solution (0.5%) was applied to the eye to deliver local anesthesia before corneal injury.

Trigeminal Ganglion Neuronal Growth Assay

Trigeminal ganglion (TG) neuronal cells were obtained and cultured as described previously. Pan, Z., Fukuoka et al., FASEB J. 27, 2756-2767 (2013). To evaluate the effect of VEGF-B on neuronal growth, TG neuronal cells were treated with 10-100 ng/ml recombinant mouse VEGF-B$^{186}$ (R&D 767-VE-010). The VEGF-B treatments were replenished every other day. Neurite formation and growth was followed up to 3 days. Inhibitions studies to determine VEGF-B—receptor interactions were carried out as follow: VEGF-B availability was competitively inhibited by treating the cells at the same time with 50 ng/ml VEGF-B and an equal molar concentration (2.6 nM) of recombinant human-soluble VEGFR1 (sVEGFR1/sFlt1, CellSciences CRF103). VEGF receptors were inhibited by using neutralizing antibodies against VEGFR1 (R&D AF471), VEGFR2 (R&D MAB4431) and Neuropilin 1 (NRP1) (R&D MAB566). TG cells were incubated in a dose dependent manner with anti-VEGFR1, anti-VEGFR2 or anti-NRP1 for 1 hour prior to the addition of 50 ng/ml VEGF-B. The tyrosine kinase domains of VEGFR2 were inhibited with specific inhibitors by incubating TG neuronal cells with 10 µM SU 1498 (Sigma T4192) or 5 nM Ki 8751 (Sigma K1265) for 1 hr before adding 50 ng/ml VEGF-B. All neurite growth was imaged with an AxioObserver Z1 fluorescence microscope in the YFP channel attached to an AxioCam HRm digital camera (Zeiss) operated by AxioVision 4.0 software. Images were analyzed using Neurolucida 9 (MBF Bioscience) a quantitative nerve tracing software.

Cell Viability Assay

The effect of VEGF-B on the survival of TG neuronal cells was evaluated with the Live/Dead Viability/Cytotoxicity kit (Invitrogen), as described in Pan, Z., Fukuoka et al., FASEB J. 27, 2756-2767 (2013).

Corneal Micropocket Assay

A sucralfate/hydron pellet impregnated with VEGF-B (100 ng/pellet) or vehicle was implanted into a corneal micropocket in anesthetized thy1-YFP mice subjected to a partial lamellar incision parallel to the limbus. Rogers, M. S. et al., *The mouse cornea micropocket angiogenesis assay*, Nature protocols 2, 2545-2550 (2007). Mice were allowed to recover for a day, after which a subset received a corneal debridement that removed a circular 2-mm region of central epithelium and the underlying sub-basal nerves. The corneas were harvested 3 days later, fixed in 4% paraformaldehyde (PFA) for 30 minutes, mounted in Vectashield medium (Vector Labs H1000) as whole mounts, and nerves imaged using the AxioObserver system as described above.

Subconjunctival Injection of VEGF

Wild type C57BL/6 and Vegf-b$^{-/-}$ mice were subject to corneal epithelial debridement as described above or left intact. A 5 ul volume containing 0.5 ng VEGF-B$^{186}$ in PBS was injected subconjunctivally, at the lateral temporal bulbar conjunctiva, using a 10-µl micro-syringe (Hamilton Co). Equal volume of 0.1% bovine serum albumin (BSA) was used in control mice. The recovery of the corneal epithelial injury was imaged at 24, 40 and 48 hours by applying 1% fluorescein solution to the corneal surface and wounds photographed under diffuse cobalt blue light attached to a slit lamp bio-microscope (Nikon FS-3, Nikon) connected to a digital camera (Canon EOS 60D). The corneal epithelial defect areas were quantified by analyzing the images with Photoshop CS4 (Adobe). Corneas were harvested after one week for immunodetection of nerves. Possible growth of blood vessel into the cornea was monitored by slit lamp examination.

Corneal Whole Mount and Immunofluorescence

Harvested corneas from thy1-YFP mice were fixed in 4% PFA for 1 hr and then stained with 4,6-diamidino-2-phenylindole (DAPI) to label nuclei before mounting. The YFP fluorescent nerves were imaged with a fluorescence microscope at the site of pellet implantation and at a site 180 degrees opposite to the pellet. Images were analyzed using Neurolucida. C57M/6 wild type and Vegf-b$^{-/-}$ mouse corneas were flat mounted and fixed as described. Pan, Z., Fukuoka et al., FASEB J. 27, 2756-2767 (2013). Samples were stained with rabbit anti-β3 tubulin antibody (Abcam 18207) overnight at 4° C., followed by alexaFluor568-conjugated goat anti-rabbit IgG (Life Technologies A11011) at room temperature for 1 hr and counter-stained with DAPI.

Corneal Nerve Regeneration Analysis

Quantification of corneal nerves regeneration was obtained from corneal wholemount images traced and analyzed with Neurolucida 9 software. Five image fields were sampled in each corneal wholemount, one at the center cornea, and the remainder at midway between the central and limbal cornea for each of four corneal quadrants. Central and peripheral cornea nerve densities were calculated and expressed as a percentage of control.

Corneal Nerve Sensation Testing

The degree of recovered nerve sensation in the injured cornea was evaluated using calibrated von Frey Hairs (North Coast Medicals). In this method the center of the cornea of un-anesthetized mouse was touched with thin filaments of ascending stiffness (0.008 to 1.4 g) until the hairs buckled and a blink response was elicited. C57BL/6 wild type and Vegf-b$^{-/-}$ mice subjected to corneal epithelial debridement and receiving subconjuntival injection of VEGF-B, as well as their respective controls, were evaluated to determine the minimal force (g) needed for a blink response. Eight mice were tested in each group in three individual experiments.

In Vitro Scratch Wound Assay

Human corneal limbal epithelial (HCLE) cells were cultured in 6-well plates until confluency as described. Pan, Z., Fukuoka et al., FASEB J. 27, 2756-2767 (2013). Cells were starved in KSFM medium (gibco 10724-011) without supplements for 24 h. Then a straight-line scratch mark was made in each well with a 200 ul pipette tip. KSFM medium supplemented with VEGF-B$^{186}$ (50 ng/ml) or EGF (10 ng/ml, Millipore 01-101) was added to the wells. Scratch areas were imaged at 0, 8, 24 and 48 hours at the same locations using the mark and find module of the Axiovision software and the wound closure analyzed by Photoshop.

VEGF-B Protein Expression

The VEGF-B protein expression was analyzed in corneal epithelia and stromas collected before surgery and at day 1, 3, and 7 following corneal debridement (n=6 corneas per time point). The level of expression was determined with the mouse VEGF-B ELISA kit (USCN Life Science Inc SEA144Mu) according to the manufacturer's protocol and as described. Pan, Z., Fukuoka et al., FASEB J. 27, 2756-2767 (2013). VEGF concentrations were normalized to total protein concentrations. Proteins were also separated in SDS-PAGE gels by PAGE electrophoresis and then transferred onto Polyvinylidene difluoride for Western blot analysis. After blocking, membranes were incubated with mouse anti-VEGF-B (Santa Cruz Biotechnology sc-80442) and rabbit anti-actin (Abcam 1801) antibodies. Membranes were washed three times in PBS, 0.1% Tween-20 and incubated with IRDye 800CW donkey anti-rabbit IgG and IRDye 700CW goat anti-mouse IgG antibodies (1:10000, Rockland Immunochemicals) for 1 hour. Blots were imaged and analyzed with Odyssey Infrared Imaging System (LI-COR).

Statistics

Data are presented as mean±SEM. The significance of differences was evaluated using analysis of variance (ANOVA) followed by post hoc test for multiple comparisons, with $P<0.05$ considered statistically significant unless otherwise stated.

Results

VEGF-B Promotes Trigeminal Ganglion Neuron Growth and Survival In Vitro

Figure 1B:
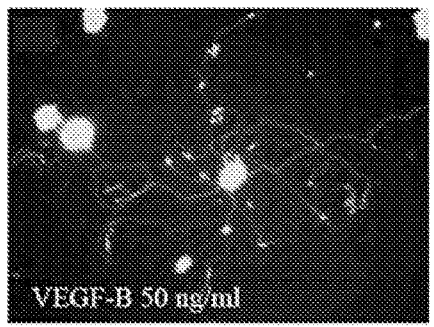
Figure 1C:
Figure 1D:
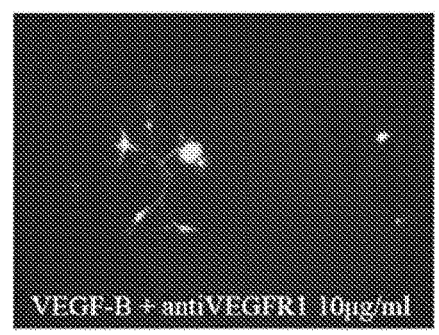
Figure 1E:
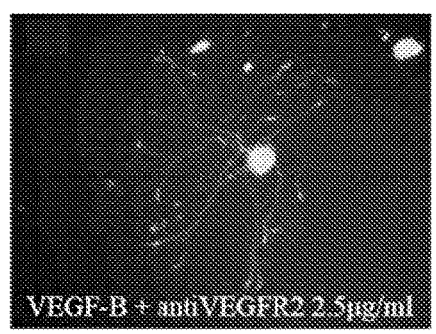
Figure 1F:
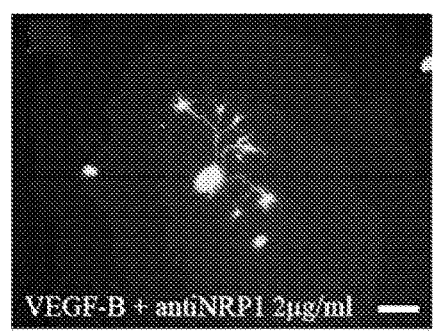
Figure 1G:
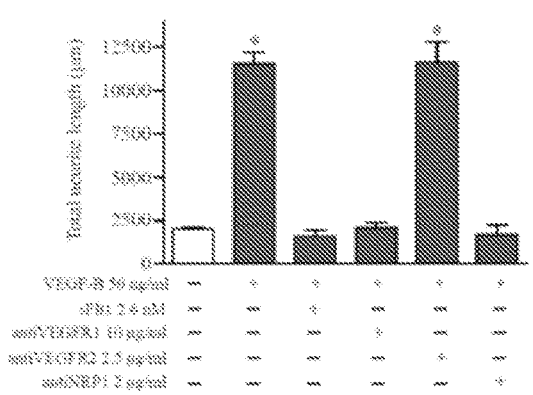
Figure 1H:
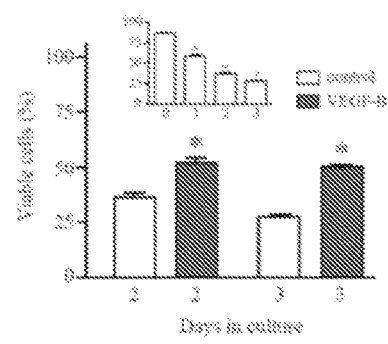
Figure 7:
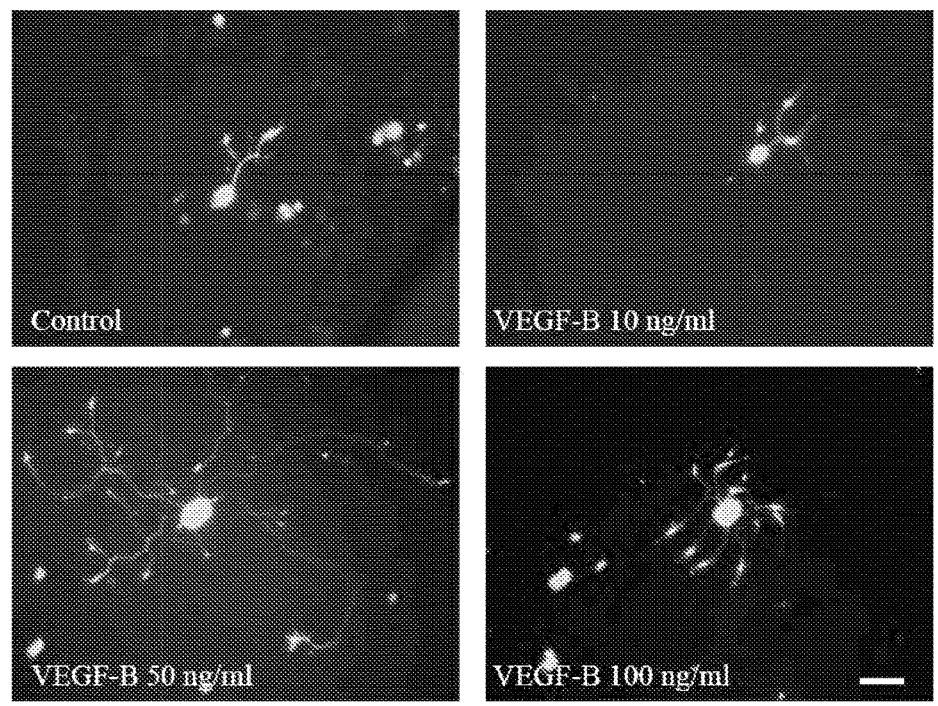
FIG. 7 includes images of cultured neurons that were analyzed for neurite growth. VEGF-B induced a dose-dependent neurite growth in cultured neurons. Isolated TG neurons where incubated in growth medium alone or with increasing concentrations of VEGF-B. After 3 days in culture the neurons were imaged and neurite growth analyzed using Neurolucida software. It was found that 50 ng/ml was the most potent dose for inducing extensive neurite elongation and branching. Data are expressed as mean±SEM (n=4). * p≤0.01. Scale bar=50 µm.
Figure 8:
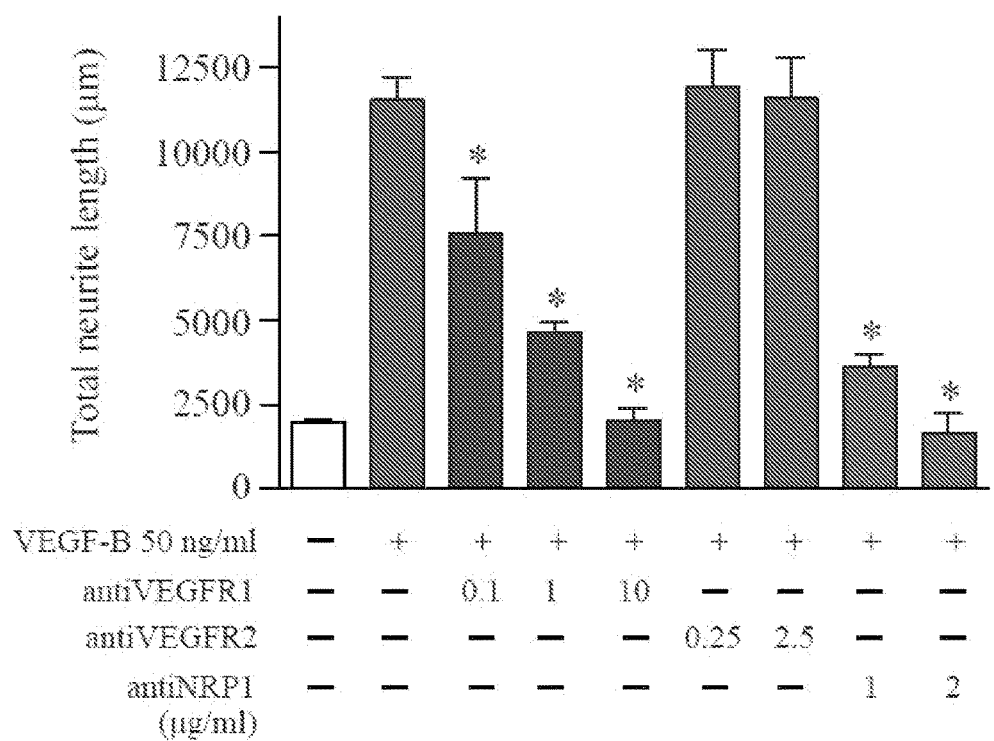
FIG. 8 shows a comparison of neurite growth for isolated TG neurons. Isolated TG neurons were preincubated for 1 hr with antibodies against VEGFR1, VEGFR2 and NRP1 in a dose dependent manner. The cells were then treated with 50 ng/ml VEGF-B and neurite growth was evaluated after 3 days. The VEGF-B induced neurite growth was inhibited dose dependently by antibodies against VEGFR1 and NRP1, but no effect was seeing in cells pre-treated with anti-VEGFR2 antibody. The comparison shows that VEGFR1 and NRP1 inhibition blocks VEGF-B induced neurite growth. Data are expressed as mean±SEM (n=3). * p≤0.01.
Figure 9A:
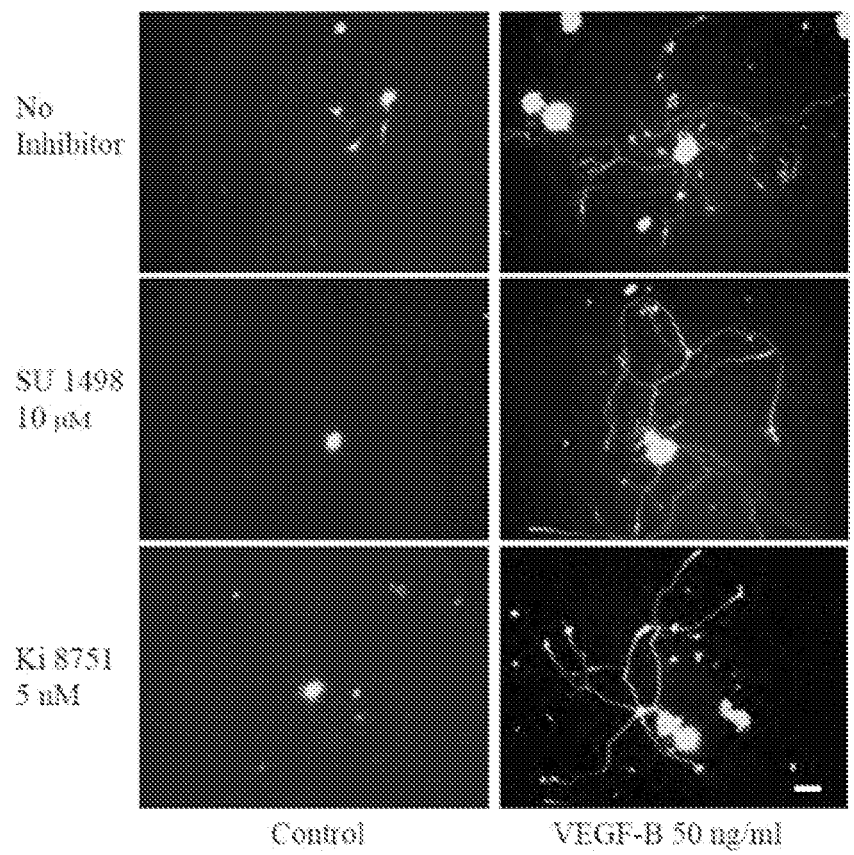
FIG. 9A includes images showing that VEGFR2 signaling is not involved in VEGF-B induced neurite growth. To confirm that VEGFR2 signaling does not play a role in VEGF-B induced neurite growth, TG neurons were pre-incubated for 1 hr with 10 µM SU1498 or 5 nM Ki8751, two specific tyrosine kinase inhibitors that targeted the tyrosine kinase domains of VEGFR2. The cells were then treated with 50 ng/ml VEGF-B and neurite growth was evaluated after 3 days. As shown in the images, there was no inhibition of neurite growth in any of the treatments.
Figure 9B:
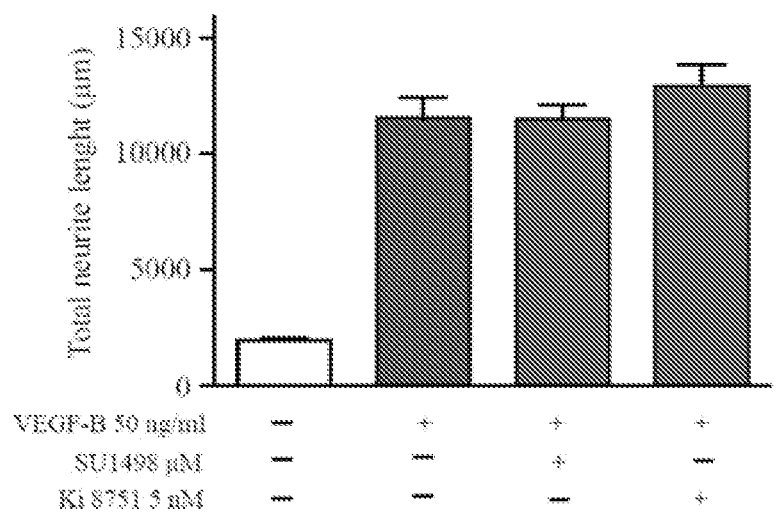
FIG. 9B further shows that there was no difference in dendrite length in the control group without inhibitors. Thus, VEGFR2 activation is not required for VEGF-B induced neurite growth. Data are expressed as mean±SEM (n=3). * p≤0.01. Scale bar=50 µm.

Peripheral nerves such as those that innervate the cornea have their origin far from the site they innervate at the trigeminal ganglia (TG). To evaluate the role of VEGF-B on promoting peripheral nerve growth, isolated TG neuronal cells were treated with different concentrations of VEGF-B. As a result, it was found that strong formation and elongation of neurites is induced when cells were incubated with 50 ng/ml VEGF-B. Specifically, at this concentration the length of neurites turned out almost four folds greater than the comparative untreated controls (FIGS. 1A, 1B and 1G). The effect of VEGF-B on inducing neurite growth is dose-dependent as shown in FIG. 7. The VEGF-B signaling leading to neurite growth was inhibited by soluble VEGFR1 (sFlt1) (FIG. 1C), antibodies against VEGFR1 (FIG. 1D) or neuropilin1 (NRP1) (FIG. 1F), but not by antibodies against VEGFR2 (FIG. 1e). Quantification of the VEGF-B induced neurite length demonstrated that both VEGFR1 and NRP1 are required for nerve growth and can be inhibited in a dose dependent manner by specific antibodies (FIG. 1G and FIG. 8). However, VEGF-B action does not require VEGFR2 activation since inhibition of the receptor via antibodies or blocking its tyrosine kinase domains with the specific inhibitor SU 1498 and Ki 8751 does not block the VEGF-B induced neurite growth (FIG. 1G and FIG. 9). TG neurons cultured without serum died in a time dependent manner and only 25% of cells survived after 3 days in culture (FIG. 1H insert). However, addition of 50 ng/ml VEGF-B as a single dose during the first day of culture was protective against neuronal death, with 50% of cells surviving at day 2 and 3 (FIG. 1H). These results demonstrate that VEGF-B not only promotes neurite growth but is also neuroprotective in vitro.

VEGF-B Induced Extensive Neurite Elongation and Branching

Figure 2A:
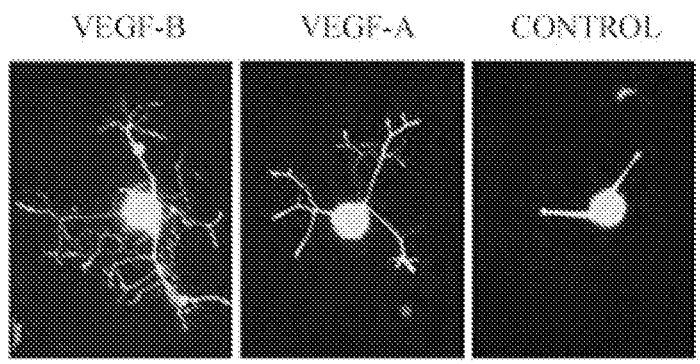
As shown in FIG. 2A, VEGF-A induced neurite growth with limited branching, while VEGF-B induced more extensive elongation and branching. Quantification of the total neurite length is shown in FIG. 2B, and demonstrates that VEGF-B induces a strong growth with higher branching area than VEGF-A. Data represent the mean±SEM, n=5, * p≤0.01. Scale bar=50 μm.
Figure 2B:
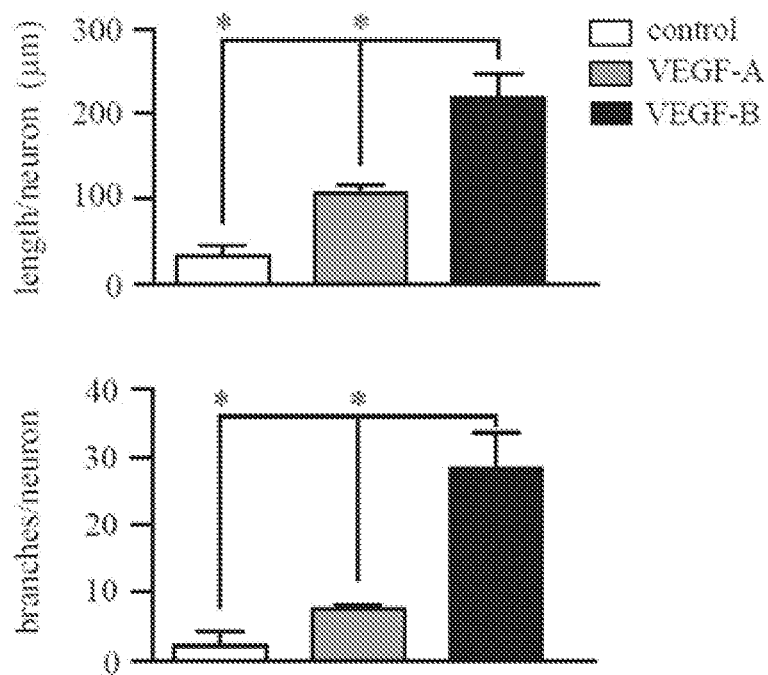
FIG. 2 shows that VEGF-B induces greater neurite elongation and branching than VEGF-A. Isolated trigeminal neurons were treated with either VEGF-A or VEGF-B at 50 ng/ml and neurite growth analyzed after three days in culture using Neurolucida software.

The effect of VEGF-B on neurite growth was significantly different from that observed previously for VEGF-A. VEGF-B induced extensive elongation and branching of the neurites while VEGF-A induces mainly neurite elongation with few branching nodes (FIG. 2A). The VEGF-B induced neurite elongation was five folds higher than untreated control and more than 2 folds higher than that induced by VEGF-A treatment (FIG. 2B). Additionally, VEGF-B treatment significantly induced neurite branching in TG neurons, the number of branching nodes was seven fold higher than untreated control and more than 4 folds than VEGF-A treated neurons (FIG. 2B).

Peripheral Nerve Injury Induces Endogenous VEGF-B Expression

Figure 3A:
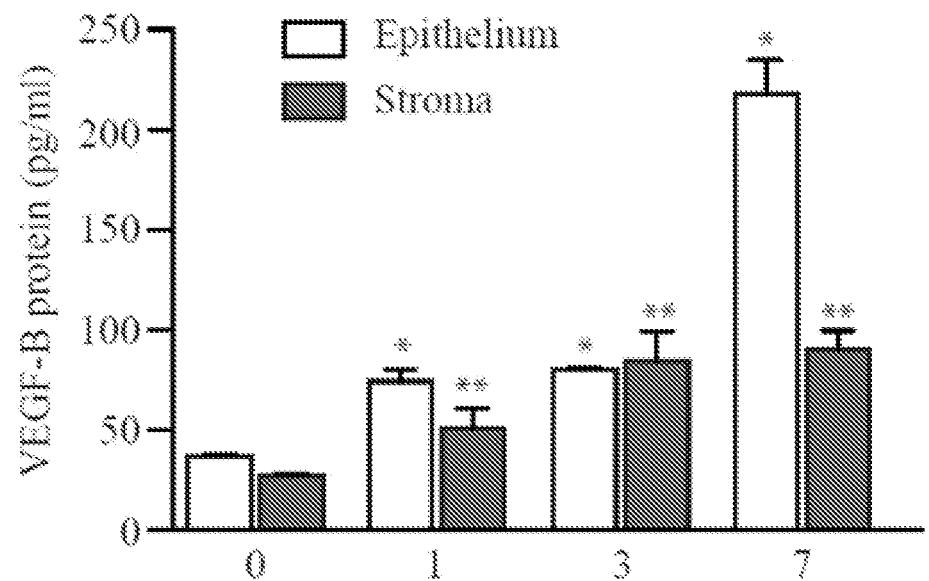
In FIG. 3A, epithelial and stroma samples were collected at the time of debridement or after 1, 3, and 7 days.
Figure 3B:
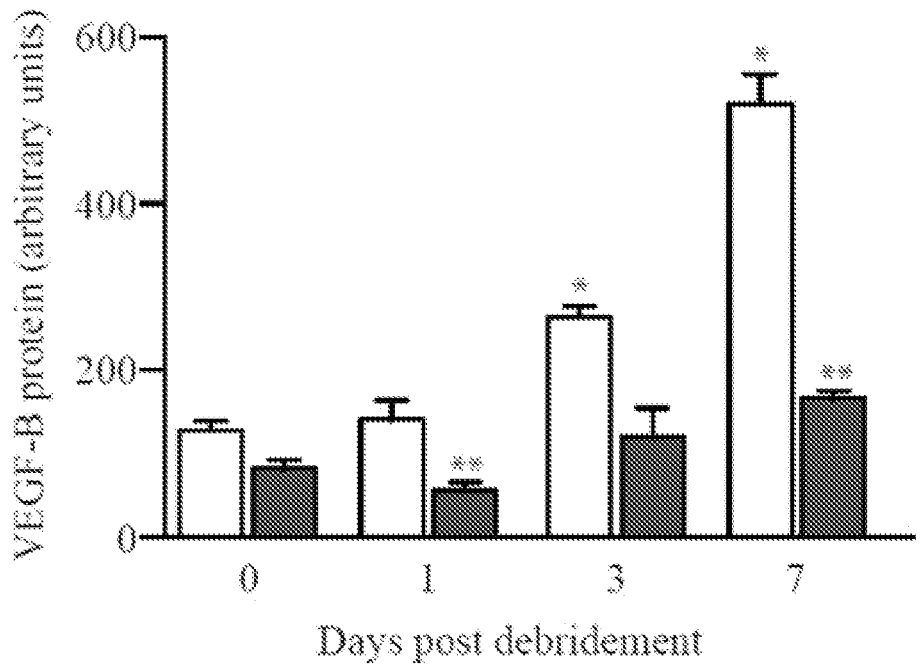
As shown in FIG. 3B, the VEGF-B protein levels steadily increased in both epithelium and stromal during all days analyzed, with higher level observed in the epithelium at day 7. Western blot analysis from these samples demonstrated that the levels of VEGF-B significantly increased after day 7 post-injury in both the epithelium and stroma. Data are expressed as mean±SEM (n=3), * p≤0.05 v/s control epithelium at day 0, ** v/s control stroma at day 0.

Previous studies have indicated that VEGF-B plays a minimal role under physiologic conditions, but may have more profound functions in disease. Carmeliet, P. & Carmen Rde, A., *VEGF ligands and receptors: implications in neurodevelopment and neurodegeneration*, Cellular Molecular Life Sciences: CMLS 70, 1727-1737 (2013). In order to determine if the expression levels of VEGF-B change in sensory nerve innervated tissues after peripheral nerve injury, a model of PNS injury was used. In that model, the sub-basal corneal epithelial plexus was removed via epithelial debridement to damage the superficial dense nerve endings. C57BL/6 wild type mice were subjected to corneal epithelial debridement and epithelial and stromal cells were collected immediately after the procedure and at 1, 3 and 7 days later to determine protein expression. VEGF-B protein levels analyzed by ELISA showed a concomitant time dependent increase with highest amounts of VEGF-B on day 7. After 1 week, the VEGF-B protein expression was 6-fold higher in epithelium and 3-fold higher in the stroma as compared to levels observed at the time of debridement (FIG. 3B). The analysis of protein expression by Western blot also showed a significantly increase of VEGF-B in both epithelium and stroma after one week of cornea injury (FIG. 3C).

Impaired Nerve Regeneration in Vegf-b$^{-/-}$ Mice is Ameliorated by VEGF-B Treatment Since peripheral nerve injury induces increased expression of VEGF-B, it was necessary to determine whether VEGF-B is required for nerve regeneration. Vegf-b$^{-/-}$ mice have no evident neurological deficit and are developmentally healthy. First, immunostaining was used to analyze the corneal nerve density and distribution in Vegf-b$^{-/-}$ and wildtype mice. No differences were found when both strains were thus compared. (FIGS. 4A and 4B, upper panels). The PNS corneal injury model described above was then used to remove via epithelial debridement the trigeminal nerve endings, and after one week, the rate of nerve regeneration back into this damaged area was measured. Greater number of growing nerve endings into the damaged area were seen in wildtype mice when compared to Vegf-b$^{-/-}$, especially in the peripheral cornea that also presented a smaller area without nerve growth (yellow dotted line). It was found that Vegf-b$^{-/-}$ mice showed significantly impaired nerve regrowth into the injured zone both at the central and peripheral areas of the cornea (FIGS. 4A and 4B, middle panels). Next examined was the ability of exogenous VEGF-B to rescue the impaired corneal nerve regeneration seen in Vegf-b$^{-/-}$, by injecting a single bolus of recombinant VEGF-B in the adjacent sub-conjunctival space immediately after the time of epithelial debridement. By one week after injury, the exogenous VEGF-B induced greater nerve regeneration in both wild type and Vegf-b$^{-/-}$ mice when compared to untreated mice (FIGS. 4A and 4B, lower panels). The quantification of the newly regenerated nerves growing into the injured zone, demonstrated that the application of VEGF-B to wild-type mice enhanced nerve regeneration in both the central and peripheral corneas, while the neuroregenerative effects of VEGF-B on Vegf-b$^{-/-}$ mice seemed confined to the peripheral cornea at the 7 day time point (FIGS. 4C and 4D).

VEGF-B Improves Functional Sensation of Injured Nerves

Figure 4E:
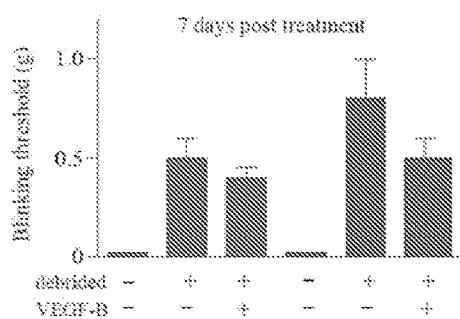
FIG. 4 includes images showing nerve density in the central and peripheral cornea. VEGF-B is required for anatomical and functional nerve regeneration. C57BL/6 and Vegf-b$^{-/-}$ mice were left untreated or subjected to corneal epithelial debridement. Mice were injected subconjuntivally with 0.5 ng of rm VEGF-B or equal volume of 0.1% BSA as control. After 1 week corneas were harvested, flat-mounted and stained with β3-tubulin antibody. Nerve density was obtained by analyzing images of the central and peripheral cornea using Neurolucida software. Normal central and peripheral nerve density and distribution was observed in both wild type and Vegf-b$^{-/-}$ untreated mice (upper panels of FIGS. 4A and 4B). In the debrided corneas, the nerves regenerated in the peripheral area in wild type but not in Vegf-b$^{-/-}$ mice as indicated by the yellow dashed lines that zoned the area without superficial nerves (middle panels of FIG. 4B), and scarce nerve regeneration was seen in the central cornea in both type of mice (middle panels of FIG. 4A). The administration of VEGF-B induced rapid nerve regeneration in the central and peripheral cornea in wild type mice, but only in the peripheral cornea in Vegf-b$^{-/-}$ nice (lower panels of FIGS. 4A and 4B). The nerve tracing analysis shows that Vegf-b$^{-/-}$ mice have a delay in nerve growth compared to wild type as shown in FIGS. 4C and 4D, and VEGF-B induced a significant increase in central nerve regeneration only in wild type mice (FIG. 4C), but significantly increased peripheral nerve regeneration in both type of mice (FIG. 4D). The functional sensation of the regenerated nerves in the ocular surface was evaluated by the von Frey Hair technique (see Materials and Methods) in both wild type and Vegf-b$^{-/-}$ mice. After 1 week post-injury, corneal sensation was similarly decreased in wild type and Vegf-b$^{-/-}$ mice (FIG. 4E). However, after 2 weeks post-injury there was a significant recovery of sensation in mice treated with VEGF-B. In wild type mice, the regenerated nerves reached the same sensation level as normal untreated control, while Vegf-b$^{-/-}$ mice demonstrated a delay in recovering complete sensation (FIG. 4F). Data are expressed as mean±SEM (n=3). * p≤0.05. Scale bar=20 µm.
Figure 4F:
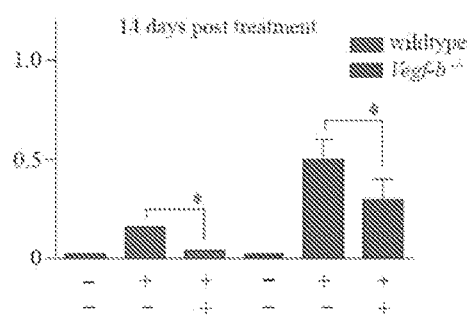

The cornea is a highly sensitive tissue, and we next investigated whether the anatomic recovery of corneal innervation in response to VEGF-B has functional consequences. For this, the corneas of mice subjected to epithelial debridement were gently touched with a set of thin filaments known as von Frey hairs, which asses the sensitivity to mechanical stimulation. After epithelial debridement and the loss of superficial sensory nerves, the mechanosensation of the ocular surface was dramatically impaired. Our analysis showed that VEGF-B treatment began to improve the functional recovery sensation of the corneas in both wild type and Vegf-b$^{-/-}$ mice after only 7 days of treatment (FIG. 4E). After 2 weeks, the VEGF-B treatment significantly improved the sensation levels in both wild type mice and Vegf-b$^{-/-}$ mice. Sensation in VEGF-B treated wild-type animals was completely restored at this time point while VEGF-B treated Vegf-b$^{-/-}$ mice had significantly improved sensation as compared to untreated Vegf-b$^{-/-}$ mice (FIG. 4F).

VEGF-B Stimulates Neuronal Growth Only in Injured Nerves

Figure 5A:
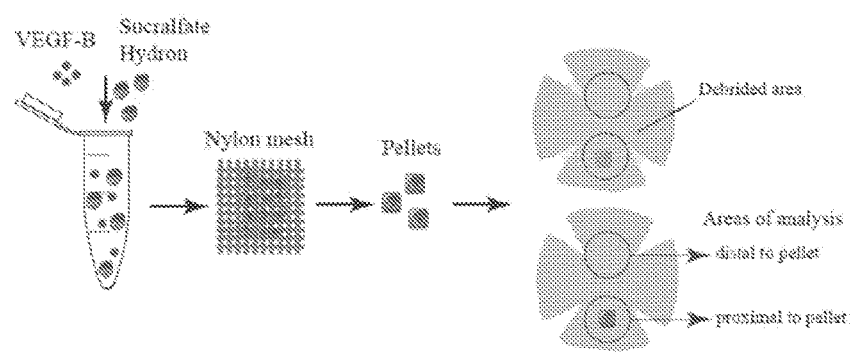
FIG. 5 is a schematic diagram showing how release of VEGF-B into the cornea selectively enhances regeneration of injured nerves. A hydron pellet containing VEGF-B or vehicle was inserted into a corneal stroma micropocket in thy1-YFP mice. The pellet ensures the slow release of VEGF-B into the cornea. One day after the procedure, a subset of mice received epithelial debridement and 3 days later corneas were collected and flatmounted for immunofluorescence analysis (FIG. 5A). Nerve growth was traced using Neurolucida software. In uninjured corneas, VEGF-B treatment did not induce any alteration in corneal nerve density or patterning (upper panels of FIG. 5B; blue gray scales bars of FIG. 5D). A significant increase in nerve regeneration was observed at the site of pellet implantation, corresponding to a site of focal injury, in animals receiving VEGF-B treatment compared to vehicle controls (upper panels of FIG. 5C; blue gray scales bars of FIG. 5E). Mice receiving VEGF-B releasing pellets that were also subjected to a superficial corneal debridement, a more extensive injury, a more profound effect was observed, with significantly increased innervation throughout sites of injury compared to control animals (lower panels of FIGS. 5B and 5C; green grayscales bars of FIGS. 5D and 5E). Data are expressed as mean±SEM (n=4). * p≤0.05. Scale bar=100 µm.
Figures 5B, 5C:
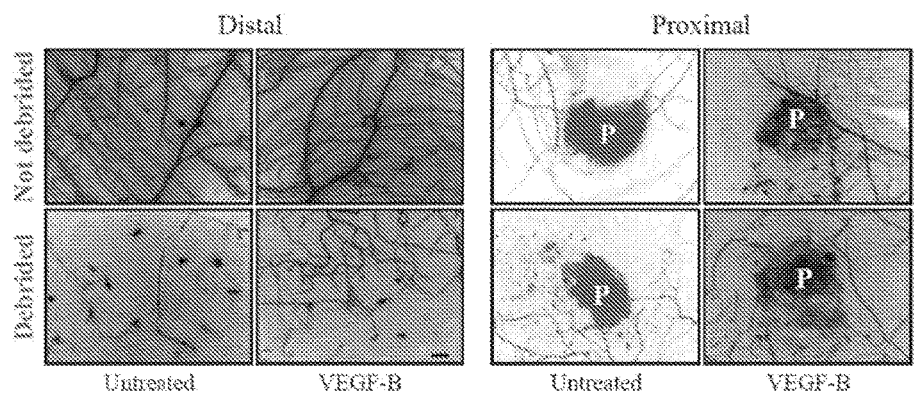
Figures 5D, 5E:
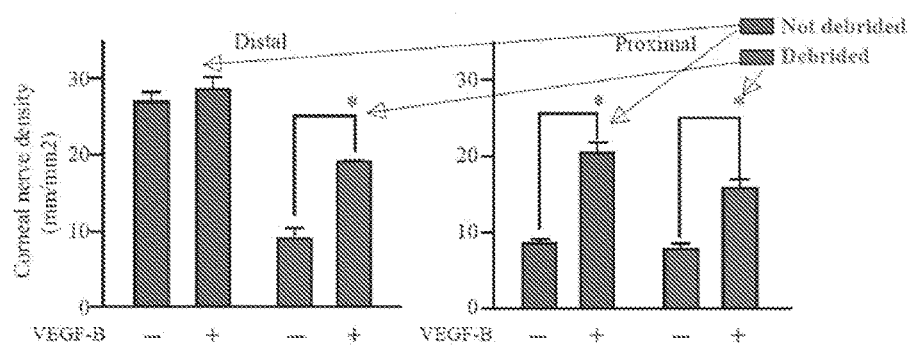

Given previous observations that VEGF-B has differential effects on intact versus injured tissues, we evaluated whether the VEGF-B induced peripheral sensory neuron regeneration was specific to injured neurons. Carmeliet, P. & Carmen Rde, A., Cellular Molecular Life Sciences: CMLS 70, 1763-1778 (2013); Poesen, K. et al., J, Neurosci, 28, 10451-10459 (2008). Thy1-YFP neurofluorescent mice were used to evaluate the in vivo effects of sustained VEGF-B release at the site of nerve injury on corneal nerve regeneration. For this we induce two types on injury in the cornea and measured the nerve growth into the damaged areas by using a nerve tracing software. To ensure the slow release of VEGF-B into the cornea, a hydron pellet containing either vehicle or VEGF-B was implanted into the corneal stroma, procedure that results in a localized injury. After recovery, a subset of mice was subjected to epithelium debridement to injury the superficial nerves resulting in a wider nerve injury (FIG. 5A). Analysis by fluorescence microcopy of cornea whole mounts taken from these animals after 3 days demonstrated that there was no alteration of corneal nerve density or patterning in the absence of injury in mice treated with vehicle or VEGF-B (FIG. 5B, upper panels; FIG. 5D, blue gray scales bars). However, there was a significant increased nerve density in response to VEGF-B at the site of pellet implantation, at which there was a limited injury (FIG. 5C, upper panels; FIG. 5E, blue gray scales bars). When mice receiving VEGF-B releasing pellets were also subjected to a superficial corneal debridement, we observed a more profound effect, with significantly increased innervation throughout sites of injury compared to control animals receiving vehicle (FIGS. 5B and 5c, lower panels; FIGS. 5D and 5E, green grayscales bars).

Figure 6A:
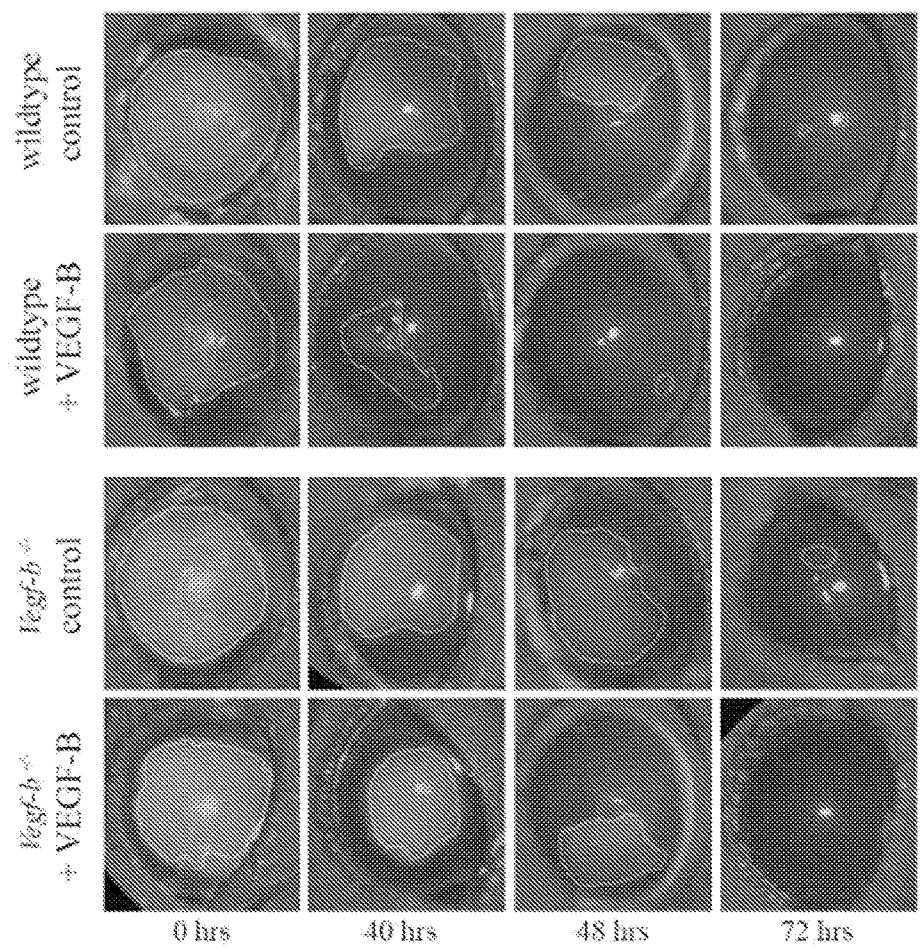
FIG. 6A includes images comparing epithelial wound closure, and showing that VEGF-B enhances corneal epithelial wound healing. Wild type C57BL/6 and Vegf-b$^{-/-}$ mice were subjected to a 2-mm central corneal epithelial debridement and immediately injected subconjunctivally with 0.5 ng of rh VEGF-B or equal volume of 0.1% BSA as a control. Fluorescein staining was used to follow the re-epithelization of the injured corneas using a slit lamp bio-microscope. In animals receiving control injections, a persistent delay in epithelial wound closure was observed in Vegf-b$^{-/-}$ when compared to wild type mice.
Figure 6B:
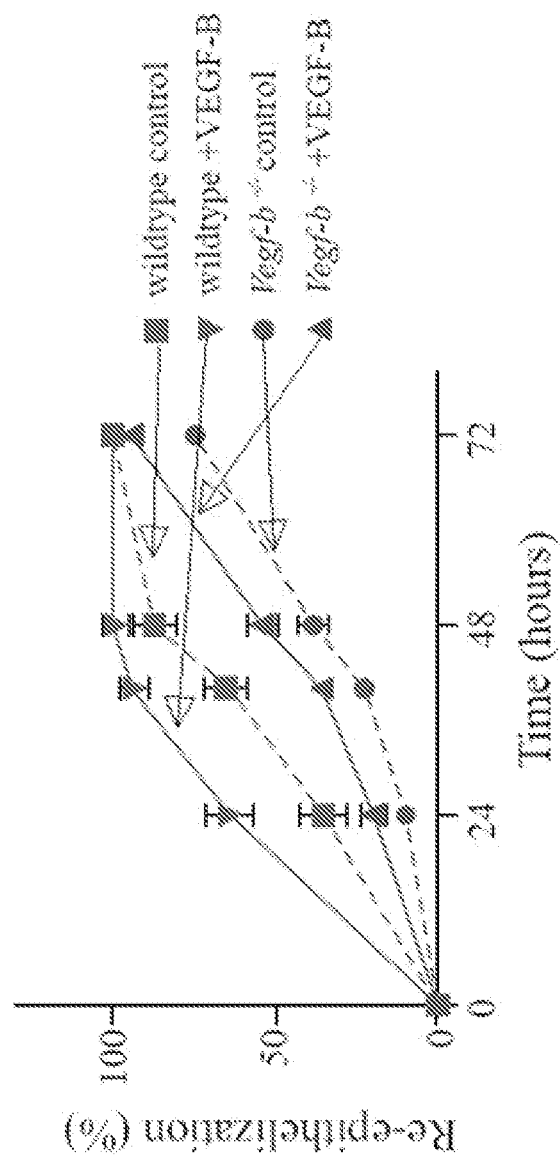
FIG. 6B shows that, in wild type mice the epithelium was almost healed at 40 h in VEGF-B treated animals, but only 60% healed in untreated mice. In Vegf-b$^{-/-}$ mice only 75% of the injured epithelium healed after 72 hr compared to almost 100% when treated with VEGF-B. Data are expressed as mean±SEM (n=3). * p≤0.01.

Impaired Corneal Epithelial Wound Healing in Vegf-b$^{-/-}$ Mice is Improved by VEGF-B The well-known trophic and functional relationship between nerves and epithelium in the cornea, lead us to study if VEGF-B has any effect on epithelial wound healing. We analyzed if VEGF-B influences the wound healing in wild type and Vegf-b$^{-/-}$ mice subjected to corneal epithelial debridement. Fluorescein staining was used to demarcate the epithelial wounded area and found that in untreated control mice, there was a delay in the re-epithelization of the injured cornea in Vegf-b$^{-/-}$ compared to wild type mice. At 48 hours, a significant area of the injured epithelium was healed in wild type mice but a larger injured area still is present in Vegf-b$^{-/-}$. Subconjunctival injection of VEGF-B clearly accelerated the epithelium regrowth in both wild type and Vegf-b$^{-/-}$ mice. There was almost complete healing in VEGF-B treated wild type mice and only half the injured area in Vegf-b$^{-/-}$ mice when compared to untreated controls at 48 hours, respectively (FIG. 6A). Quantification analysis of the wounded areas showed that in wild type mice, VEGF-B treatment induced 90% epithelial healing at 40 hours, while untreated mice displayed only 60% closure. Similarly, VEGF-B improved epithelial wound healing in Vegf-b$^{-/-}$ with over 90% closure at 72 hours compared to 70% closure in untreated mice (FIG. 6B).

Figure 10A:
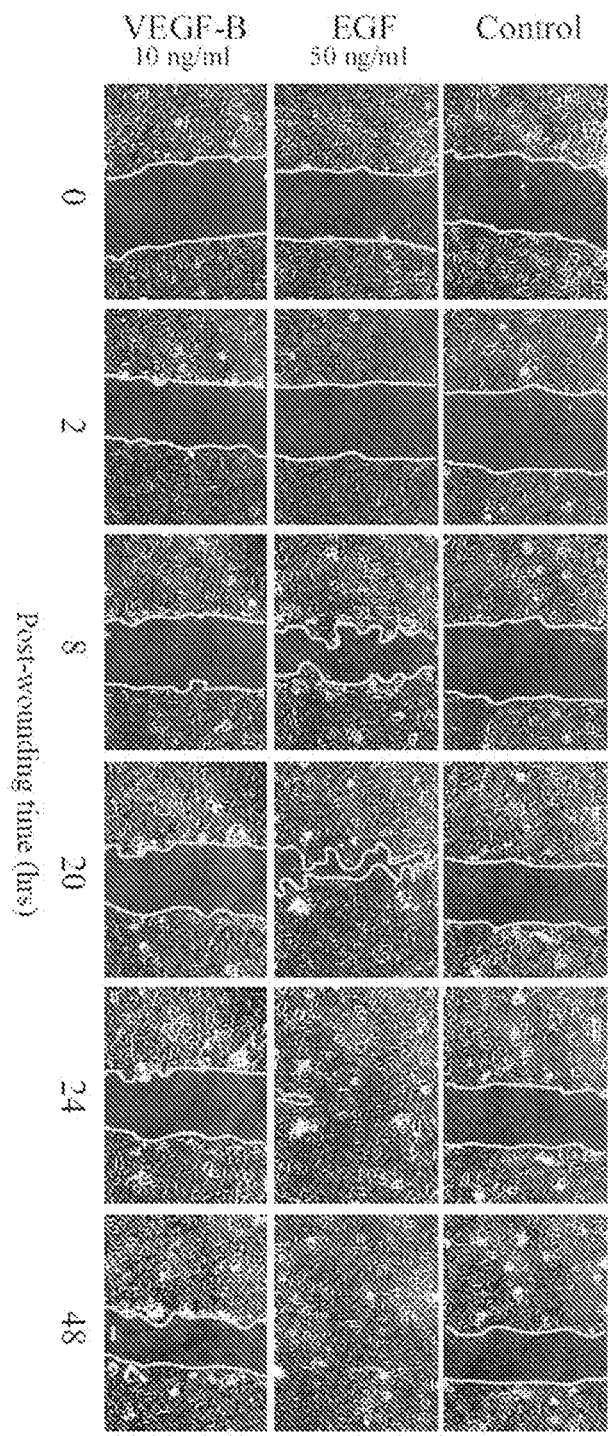
FIG. 10A includes images of cell growth observed in scratched areas at various time intervals, which show that VEGF-B does not directly induce epithelial wound healing. A scratch was made on human corneal limbal epithelial (HCLE) grew to confluence in KSFM (see Material and Methods). Cells were cultured in absence or presence of 50 ng/ml VEGF-B or 10 ng/ml epidermal growth factor (EGF). The cell growth into the scratch areas was imaged at 0, 2, 8, 20, 24 and 48 hr at the same locations in the culture using an automated phase-contrast microscope.
Figure 10B:
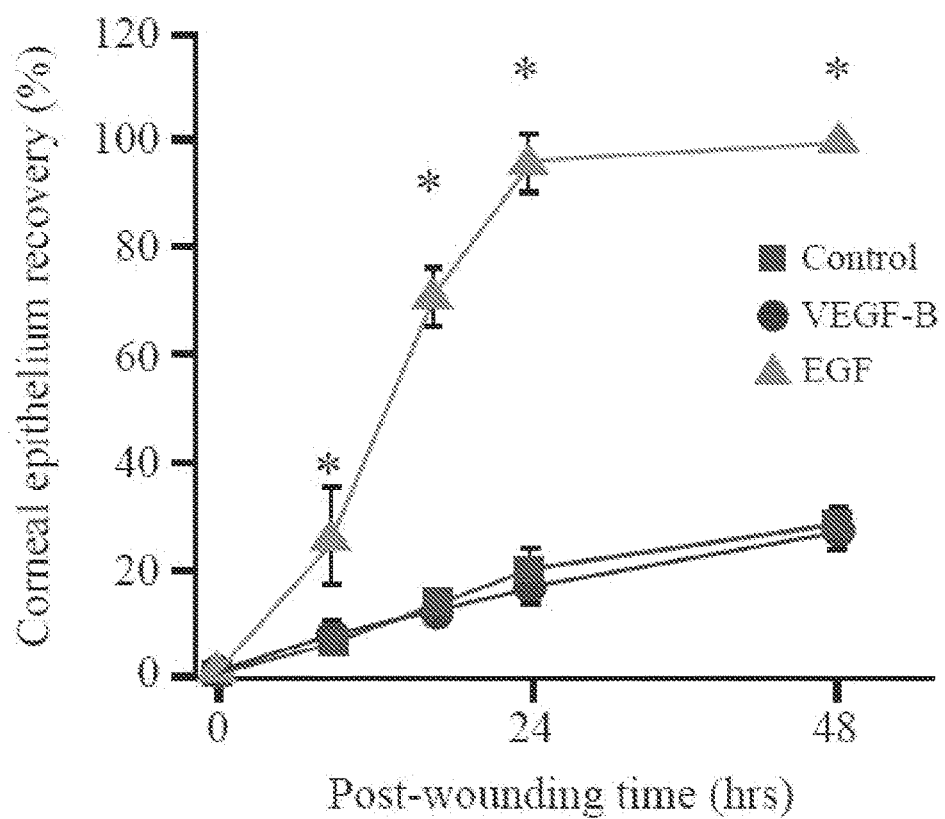
FIG. 10B is a quantitative comparison of the respective corneal epithelium recovery times, showing that VEGF-B has no effect on inducing HCLE cell growth compared to untreated control. Quantification demonstrated that EGF induced cell growth into the scratch area as soon as 8 hr post-treatment with complete confluence at 24 hr. However, VEGF-B did not influence re-epithelization of the scratched area. Data are expressed as mean±SEM (n=3). * p≤0.01. Scale bar=50 µm.

Given the pleiotropic roles of VEGF-B, we analyzed if the faster re-epithelization seen upon VEGF-B administration is a direct effect on the epithelial cells or due to indirect effects of VEGF-B on corneal nerve regeneration and the subsequent trophic action of these nerves on the epithelium. Human corneal limbal epithelial cells were cultured to confluency and made an epithelial injury using a scratch wound assay. Cells treated with VEGF-B showed similar re-epithelization compared to untreated control cells after 48 hr incubation, whereas cells treated with epidermal growth factor, a known inducers of epithelial cells proliferation, completely closed the scratch area before 24 hours (FIG. 10). Thus, VEGF-B has no direct effect on the corneal epithelial wound healing and the effect induced by VEGF-B in vivo is likely due to the trophic influence of regenerated corneal nerves.

Figure 13A:
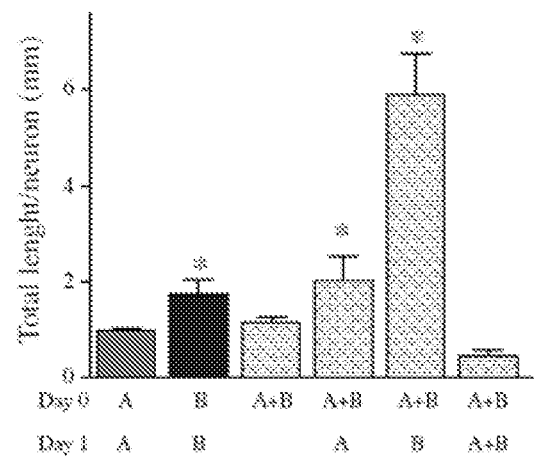
FIG. 13 shows a comparison of the neuron lengths (FIG. 13A) and the neuronal branching (FIG. 13B) observed as a result of various combinations of VEGF ligands, rather than the ligands being given separately. TG neurons were treated with different combinations of VEGF-A and VEGF-B. As shown, combinations of VEGF ligands induced responses different from ligands that were given separately. Notably, treatment of neurons with both ligands on the first day of incubation, followed by VEGF-B treatment afterwards, produced the best neurite growth in culture.
Figure 13B:
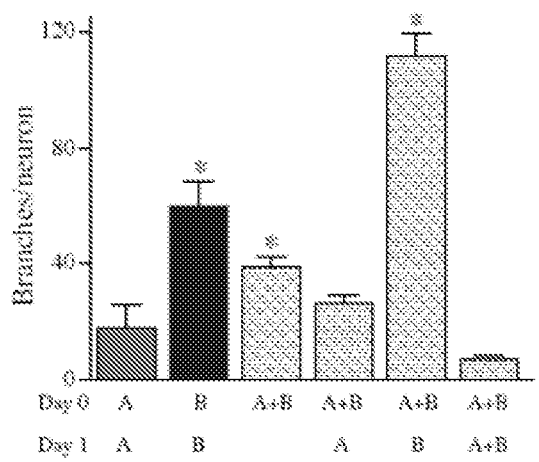

Combinations of VEGF Ligands Demonstrate Synergistic Neuronal Effects that are not Merely Additive Effects of the Ligands Applied Separately In order to optimize the effects of VEGF-A and VEGF-B on corneal nerve growth, both ligands (VEGF-B and VEGF-A) were applied in combination to isolated trigeminal ganglia (TG) neurons. Surprisingly, when administered in combination, neuronal growth was less robust than that seen when either VEGF-A or VEGF-B were administered individually (FIG. 13A). However, the combination of VEGF-A and VEGF-B was not "inferior" to the separate ligands in all instances. Previous findings had indicated that, following injury, the expression of VEGF-A preceded that of VEGF-B at the transcriptional and protein level. Given these findings, the temporal application of the VEGF ligands was now reversed. The results demonstrated that, when the VEGF-A/VEGF-B combination was supplied to TG neurons on the first culture day, a subsequent application of either VEGF-A or VEGF-B unexpectedly surpassed that of the ligands delivered separately (FIG. 13B). Moreover, simple and persistent application of combined VEGF-A and VEGF-B resulted in actually decreasing neuronal growth.

Figure 14:
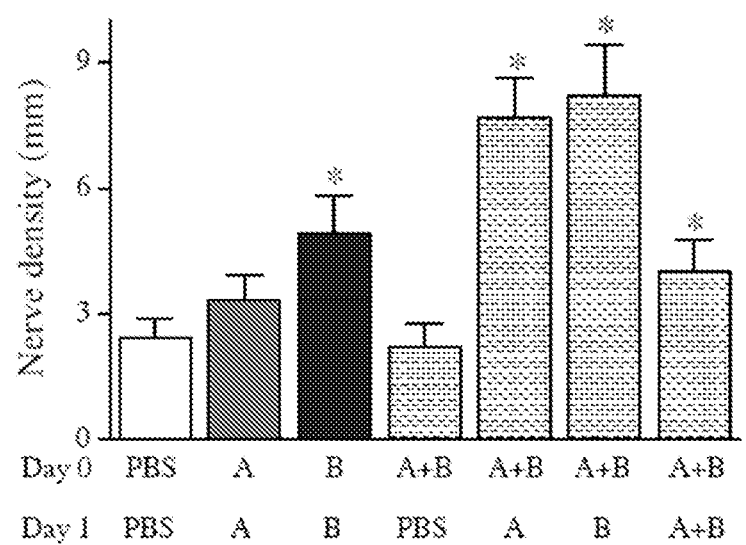
FIG. 14 shows a comparison of nerve densities resulting from various combinations of VEGF ligands. Thy-1-YFP mice were subjected to cornea epithelium debridement to ablate the superficial nerve endings that innervate the cornea Immediately after injury, the mice were treated with different combinations of VEGF-A and VEGF-B. As shown, combinations of VEGF ligands induce greater nerve regeneration in vivo. Notably, treatment with both ligands on the first day of incubation, followed by VEGF-A or VEGF-B afterwards resulted in faster and greater nerve regeneration.

The observed effects were also recapitulated in vivo. Thy-1-YFP neurofluorescent mice were used to induce a corneal epithelium injury that results in ablation of the superficial nerve endings of the cornea. The mice were then treated with different combinations of VEGF-A and VEGF-B, and nerve regeneration was analyzed after two weeks post-injury. As documented in previous publications, both VEGF-A and VEGF-B induced greater nerve regeneration when administered separately. However, when administered simultaneously, their effect decreased to control level, but was further enhanced if the treatment was followed by administration of a single ligand (FIG. 14). As seen in vitro, administration of VEGF-A+VEGF-B, followed by a second administration of VEGF-B afterwards, induced the best neuronal growth that in vivo resulted in larger nerve density (FIG. 14).

DISCLAIMER

The individual features of the invention are not limited to the described combinations of features based on the exemplary embodiments described herein. It should also be understood that various principles of the invention have been described by way of illustrative embodiments. However, many combinations and modifications of the above described methods and components, as well as compositions used in the practice of the claimed invention, in addition to those not specifically described, may be varied without departing from the scope of the disclosure. Such variations and modifications could be ascertained by persons skilled in the art using no more than routine experimentation, and are therefore also encompassed by the present disclosure.

What is claimed is:

1. A method for treating peripheral nerve damage in an eye of a subject, comprising:
   administering VEGF-B to the subject by topical application to the eye having the nerve damage in an amount effective to treat the peripheral nerve damage by stimulating nerve growth at a location of the nerve damage.

2. The method according to claim 1, wherein the VEGF-B is administered to the subject in combination with VEGF-A.

3. The method according to claim 1, wherein the VEGF-B is administered as a protein.

4. The method according to claim 2, wherein the VEGF-B and the VEGF-A are administered as proteins.

5. The method according to claim 1, wherein the VEGF-B is administered to the subject in a pharmaceutical composition by topical application at a location of the nerve damage.

6. The method according to claim 1, further comprising, after the administering of the VEGF-B, a second topical administration to the eye of a subject of a second effective amount of VEGF-B or of VEGF-A.

7. The method according to claim 2, further comprising, after the administering of the VEGF-B, a second topical administration to the eye of a subject of a second effective amount of VEGF-B or of VEGF-A.

8. The method according to claim 7, wherein the second administration is of a second effective amount of VEGF-B.

9. The method according to claim 8, wherein the second administration is after a time of from 1 or more minutes to 2 days after the first administration of VEGF-B.

10. The method according to claim 1, wherein the peripheral nerve damage is neuritis.

11. The method according to claim 1, wherein the VEGF-B is administered as a nucleic acid encoding VEGF-B protein.

12. A method for treating ocular nerve damage in an eye of a subject, comprising:
    administering an effective amount of VEGF-B to a subject by topical administration to the eye suffering from the ocular nerve damage.

13. The method according to claim 12, wherein the ocular nerve damage is a result of trauma caused by an accident or surgery.

14. The method according to claim 12, wherein the ocular nerve damage is in the cornea.

15. The method according to claim 12, wherein the ocular damage is neuritis.

16. The method according to claim 12, comprising administering the VEGF-B to the subject in combination with an effective amount of VEGF-A.

17. The method according to claim 16, further comprising, after the administering of the VEGF-B in combination with VEGF-A, a second topical administration to the eye of a subject of a second effective amount of VEGF-B or of VEGF-A.

18. The method according to claim 17, wherein the second administration is after a time of from 1 or more minutes to 2 days after the first administration of VEGF-B.

19. The method according to claim 17, wherein the second administration is of a second effective amount of VEGF-B.

20. The method according to claim 17, wherein the second administration is of a second effective amount of VEGF-A.

21. The method according to claim 12, wherein the VEGF-B is administered as a nucleic acid encoding VEGF-B protein.

* * * * *